(12) United States Patent
Nelson Mock et al.

(10) Patent No.: US 11,596,759 B2
(45) Date of Patent: Mar. 7, 2023

(54) METHODS AND SYSTEMS FOR A MEDICAL GAS DELIVERY MODULE

(71) Applicant: General Electric Company, Schenectady, NY (US)

(72) Inventors: Kristen Elizabeth Nelson Mock, Lake Mills, WI (US); Donald Charles Meyferth, Sun Prairie, WI (US)

(73) Assignee: General Electric Company, Schenectady, NY (US)

( * ) Notice: Subject to any disclaimer, the term of this patent is extended or adjusted under 35 U.S.C. 154(b) by 1120 days.

(21) Appl. No.: 16/218,370

(22) Filed: Dec. 12, 2018

(65) Prior Publication Data
US 2020/0188624 A1 Jun. 18, 2020

(51) Int. Cl.
*F17D 1/04* (2006.01)
*A61M 16/10* (2006.01)
(Continued)

(52) U.S. Cl.
CPC .... *A61M 16/1015* (2014.02); *A61M 16/0051* (2013.01); *A61M 16/024* (2017.08);
(Continued)

(58) Field of Classification Search
CPC ............ A61M 16/1015; A61M 16/024; A61M 16/0051; A61M 16/104; A61M 16/12;
(Continued)

(56) References Cited

U.S. PATENT DOCUMENTS

| | | | | |
|---|---|---|---|---|
| 4,535,766 A | * | 8/1985 | Baum | A61M 16/0051 128/204.23 |
| 5,335,653 A | * | 8/1994 | Blomqvist | A61M 16/0627 128/200.24 |

(Continued)

FOREIGN PATENT DOCUMENTS

| | | |
|---|---|---|
| CN | 104303127 B | 4/2017 |
| CN | 106338005 B | 11/2018 |

(Continued)

OTHER PUBLICATIONS

Lye, A. et al., "Oxygen Contamination of the Nitrous Oxide Pipeline Supply," Anaesthesia and Intensive Care, vol. 26, No. 2, Apr. 1998, 3 pages.

(Continued)

*Primary Examiner* — Minh Q Le
(74) *Attorney, Agent, or Firm* — McCoy Russell LLP

(57) ABSTRACT

Various methods and systems are provided for controlling a supply of medical gas to a gas delivery system, such as an anesthesia machine, via a medical gas delivery module. In one example, a method includes supplying a medical gas from a pipeline gas supply source to a gas delivery system via a first conduit, measuring a quality of the medical gas in the first conduit, comparing the measured quality to an allowable range, switching to an alternative gas supply source for supplying the medical gas to the gas delivery system and communicating a pipeline gas supply fault in response to the measured quality being outside of the allowable range, and continuing supplying the medical gas (Continued)

to the gas delivery system from the pipeline gas supply source in response to the measured quality being inside of the allowable range.

15 Claims, 11 Drawing Sheets

(51) Int. Cl.
*A61M 16/00* (2006.01)
*A61M 16/12* (2006.01)
*F17D 3/01* (2006.01)
*F17D 3/18* (2006.01)

(52) U.S. Cl.
CPC .......... *A61M 16/104* (2013.01); *A61M 16/12* (2013.01); *F17D 1/04* (2013.01); *F17D 3/01* (2013.01); *F17D 3/18* (2013.01); *A61M 2016/0027* (2013.01); *A61M 2016/1035* (2013.01); *A61M 2202/0208* (2013.01); *A61M 2202/0225* (2013.01); *A61M 2202/0283* (2013.01)

(58) Field of Classification Search
CPC .. A61M 2016/0027; A61M 2016/1035; A61M 2202/0208; A61M 2202/0225; A61M 2202/0283; F17D 1/04; F17D 3/01; F17D 3/18
USPC ... 137/2, 487.5, 599.07, 599.03, 602, 625.4; 118/694; 128/202.22, 207.12
See application file for complete search history.

(56) References Cited

U.S. PATENT DOCUMENTS

| | | | | |
|---|---|---|---|---|
| 7,194,863 | B2* | 3/2007 | Ganev | F02C 9/28 60/773 |
| 9,616,193 | B2* | 4/2017 | Acker | A61M 16/0003 |
| 9,690,304 | B2 | 6/2017 | Downie | |
| 2008/0078385 | A1* | 4/2008 | Xiao | A61M 16/14 128/203.26 |
| 2009/0121592 | A1* | 5/2009 | De Nando | A61B 50/10 312/209 |
| 2009/0194103 | A1* | 8/2009 | Thom | A61M 16/104 128/203.12 |
| 2010/0078017 | A1* | 4/2010 | Andrieux | A61M 16/161 128/200.24 |
| 2012/0258655 | A1* | 10/2012 | Carnell | E04H 3/08 454/284 |
| 2014/0150786 | A1* | 6/2014 | Gongmin | A61M 16/12 128/204.21 |
| 2016/0151601 | A1* | 6/2016 | Cardelius | A61M 16/104 128/203.14 |
| 2016/0252900 | A1* | 9/2016 | Junk | G05B 23/0256 702/125 |
| 2017/0368293 | A1* | 12/2017 | Nishiwaki | A61M 16/104 |
| 2019/0358418 | A1* | 11/2019 | Sarkela | A61M 16/104 |
| 2020/0147338 | A1* | 5/2020 | Lacey | A61M 16/208 |
| 2020/0232604 | A1* | 7/2020 | Franz | F17C 13/025 |
| 2021/0299376 | A1* | 9/2021 | Gleim | H04W 4/80 |

FOREIGN PATENT DOCUMENTS

| | | |
|---|---|---|
| FR | 2957806 A1 | 9/2011 |
| JP | 0894000 A | 4/1996 |

OTHER PUBLICATIONS

Hay, H., "Contamination of piped medical gas supply with water," European Journal of Anaesthesiology, vol. 17, No. 8, Aug. 2000, 3 pages.
Kandemir, T. et al., "Sudden Appearance of Water in Flowmeter During Air/Oxygen and Sevoflurane Anaesthesia," Turkish Journal of Anaesthesiology and Reanimation, vol. 43, No. 1, Feb. 2015, Published Online Sep. 9, 2014, 3 pages.
FR2957806 Espacenet English translation of Abstract; retrieved via on-line search Jun. 23, 2020.
JP0894000 Espacenet English translation of Abstract; retrieved via on-line search Jun. 23, 2020.
PCT application PCT/US2019/065628 filed Dec. 11, 2019, International Search Report/Written Opinion dated Apr. 22, 2020, 28 pages.
CN patent application 201980081632.6 filed Dec. 11, 2019—Office Action dated Jul. 5, 2022; 9 pages.
CN106338005 English Abstract; Espacenet search results Sep. 30, 2022; 1 page.

* cited by examiner

METHODS AND SYSTEMS FOR A MEDICAL GAS DELIVERY MODULE

FIELD

Embodiments of the subject matter disclosed herein relate to gas delivery systems, and more particularly, to devices for monitoring medical gas supplied to the gas delivery systems.

BACKGROUND

Healthcare facilities, such as hospitals, include medical gas pipelines that deliver different types of medical gases (e.g., oxygen, nitrogen, carbon dioxide, and nitrous oxide) to various locations throughout the facility. For example, the medical gas pipelines may supply the medical gases from source equipment (e.g., gas tanks, pumps, compressors, dryers, receivers, and manifolds) at a centralized location to gas delivery systems at a patient care location via a network of pipes and service outlets. The gas delivery system may in turn provide medical gas to a patient, such as to provide anesthesia (e.g., when the gas delivery system is configured as an anesthesia machine) and/or to assist in respiration (e.g., when the gas delivery system is configured as a ventilator).

BRIEF DESCRIPTION

In one embodiment, a method for a medical gas delivery module includes supplying a medical gas from a pipeline gas supply source to a gas delivery system via a first conduit, measuring a quality of the medical gas in the first conduit, comparing the measured quality to an allowable range, switching to an alternative gas supply source for supplying the medical gas to the gas delivery system and communicating a pipeline gas supply fault in response to the measured quality being outside of the allowable range, and continuing supplying the medical gas to the gas delivery system from the pipeline gas supply source in response to the measured quality being inside of the allowable range.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1A:
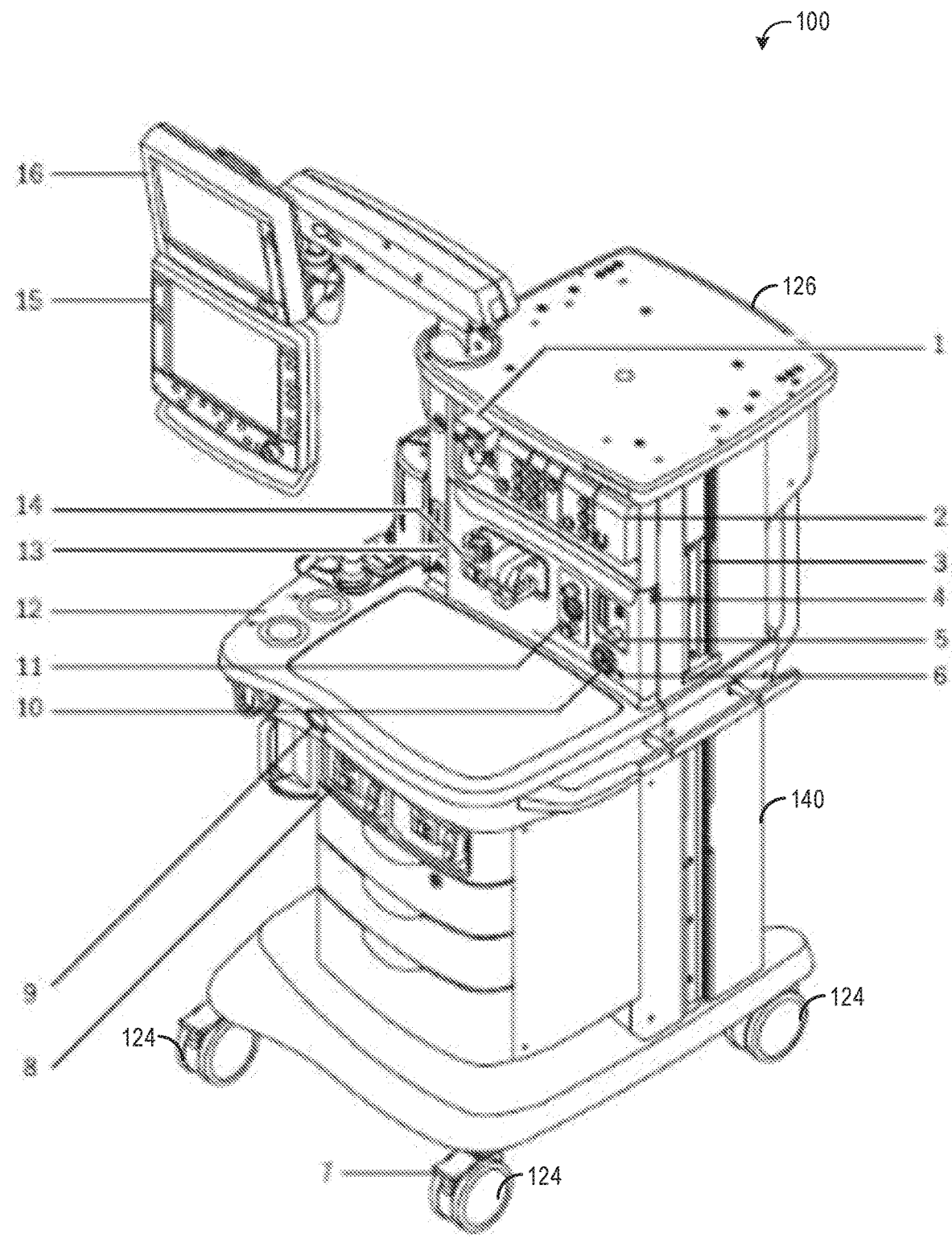
FIGS. 1A, 1B, and 1C show a first front perspective view, a second front perspective view, and back perspective view, respectively, of an anesthesia machine.

The following description relates to various embodiments for monitoring and controlling a flow of medical gas delivered to a gas delivery system, such as an anesthesia machine or ventilator. The gas delivery system may in turn provide the medical gas to a patient. During operation, the gas delivery system typically receives the medical gas (e.g., oxygen, nitrogen, nitrous oxide, air, or carbon dioxide) from a centralized location that is remote from a patient care location, and thus, remote from the gas delivery system. For example, the medical gas may be carried from the centralized location to the patient care location via a medical gas pipeline. In some examples, the medical gas delivered by the medical gas pipeline may become contaminated, such as by water vapor or oil. In other examples, the medical gas pipeline may deliver the wrong gas, such as after pipeline maintenance is performed (e.g., due to a cross-connect). The centralized location may include gas quality monitoring devices that monitor for gas contaminants and gas composition and alert personnel at the centralized location to any deviations in gas quality. However, these devices do not actively prevent the contaminated or wrong medical gas from being delivered to the gas delivery system and to the patient. For example, the personnel at the centralized location must react to alarms output by the gas quality monitoring devices to limit the extent of equipment and patient exposure to the contaminated or wrong medical gas. Further, any deviations in gas quality may not be communicated to the patient care location, and thus, an operator of the gas delivery system may continue to flow the contaminated or wrong medical gas through the gas delivery system. The contaminated gas may degrade components of the gas delivery system, for example, leading to gas delivery system shutdown, high maintenance costs, and increased operator frustration. Further still, the operator of the gas delivery system may not know the source of the degradation that resulted in the gas delivery system shutting down. For example, a diagnostic log of the gas delivery system may state that a valve is degraded, but it may not have any information about what caused the valve degradation.

Thus, according to embodiments disclosed herein, a medical gas delivery module is provided to proactively prevent the contaminated or wrong medical gas from flowing through the gas delivery system. For example, the medical gas from the medical gas pipeline may first flow through the medical gas delivery module before flowing to the gas delivery system. The medical gas delivery module may include one or more sensors upstream of an inlet to the gas delivery system to detect water vapor (e.g., via a humidity sensor), chemical or hydrocarbon contamination (e.g., via a volatile organic compound or hydrocarbon sensor), particulate contamination (e.g., via a particulate matter sensor), and/or gas composition (e.g., via an oxygen sensor) to confirm that the gas supplied by the medical gas pipeline to the gas delivery system is clean, dry, and of an expected composition. A controller of the medical gas delivery module may monitor signals received from the one or more sensors, and if contamination or a deviation from the expected composition is detected, the controller may block the flow of the gas from the medical gas pipeline and automatically switch to a predetermined alternative gas supply, such as via coordinated valve control.

The embodiments disclosed herein may provide several advantages. For example, the embodiments disclosed herein may provide for an uninterrupted supply of clean, dry medical gas of the expected composition without human intervention, thereby limiting equipment and patient exposure to a contaminated or wrong medical gas. As another example, the controller of the medical gas delivery module may communicate a pipeline gas supply fault to the operator of the gas delivery system, a controller of the gas delivery system, and a remote error log so that pipeline supply errors can be tracked. For example, tracking the errors may enable cross-correlation between pipeline supply errors and gas delivery system degradation.

Further still, the embodiments disclosed herein may provide additional advantages. As one example, monitoring medical gas composition via the medical gas delivery module allows for active gas delivery system compensation when the medical gas is oxygen gas sourced from an oxygen concentrator instead of a pre-filled cylinder. For example, the oxygen concentrator may be used to generate the oxygen gas on-site, resulting in gas that is approximately 92-93% oxygen (versus 100% oxygen from pre-filled cylinders). The controller of the medical gas delivery module may communicate the measured concentration of oxygen to the controller of the gas delivery system, and the controller of the gas delivery system may use the measured concentration to adjust calibration equations for downstream flow delivery. Thus, an accuracy of the concentration of oxygen delivered to the patient by the gas delivery system may be increased.

Figure 1B:
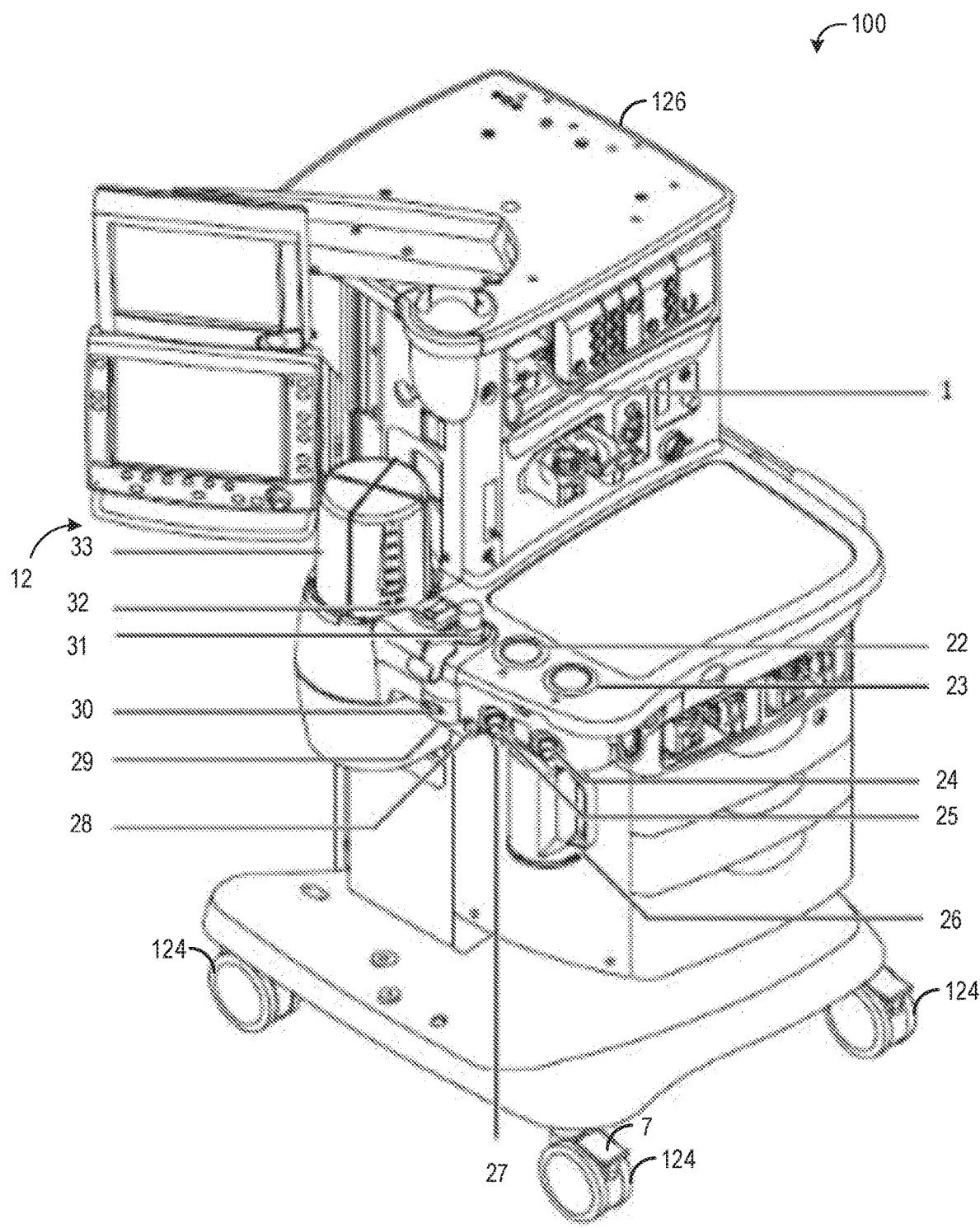
Figure 1C:
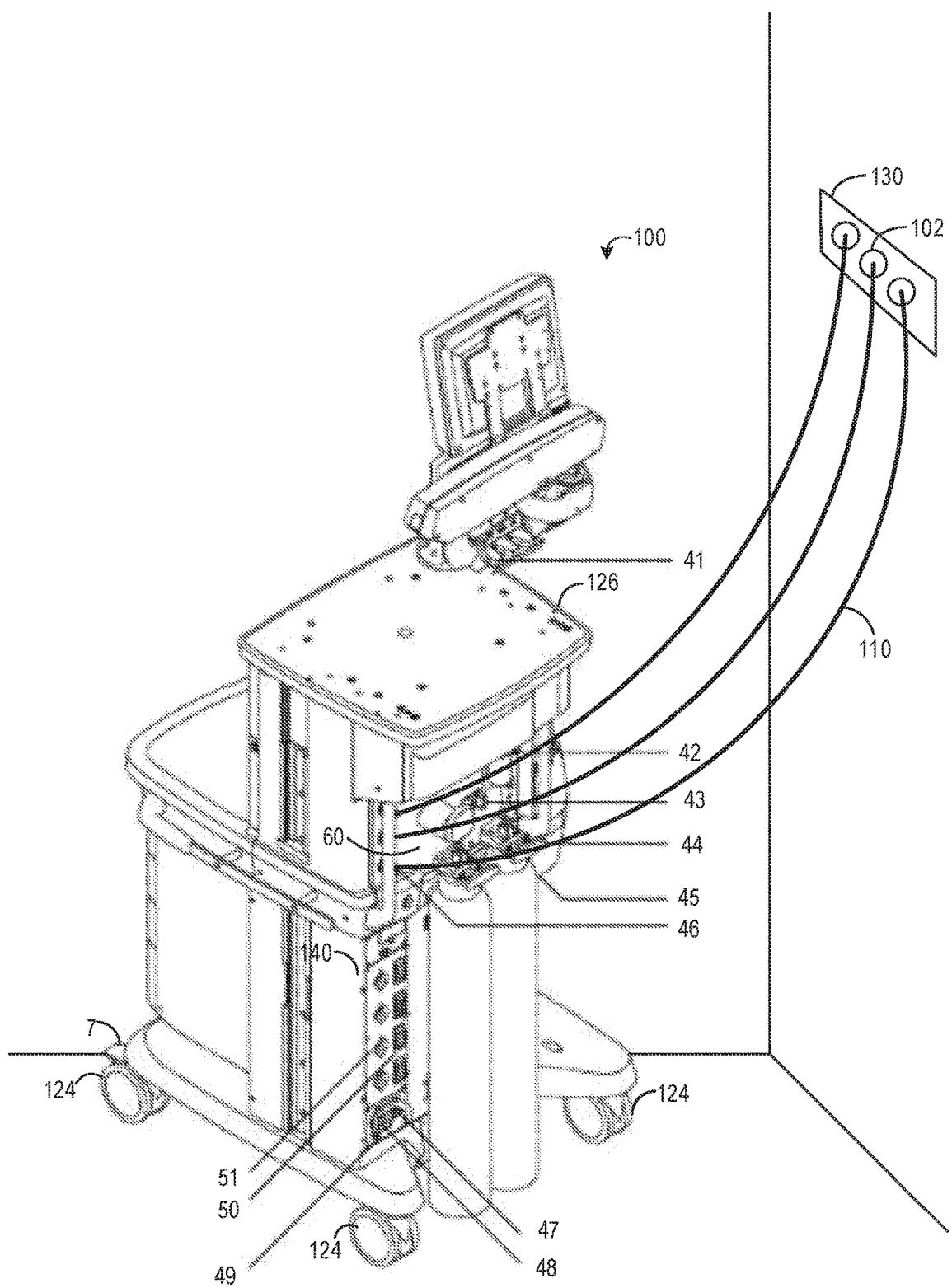
Figure 2:
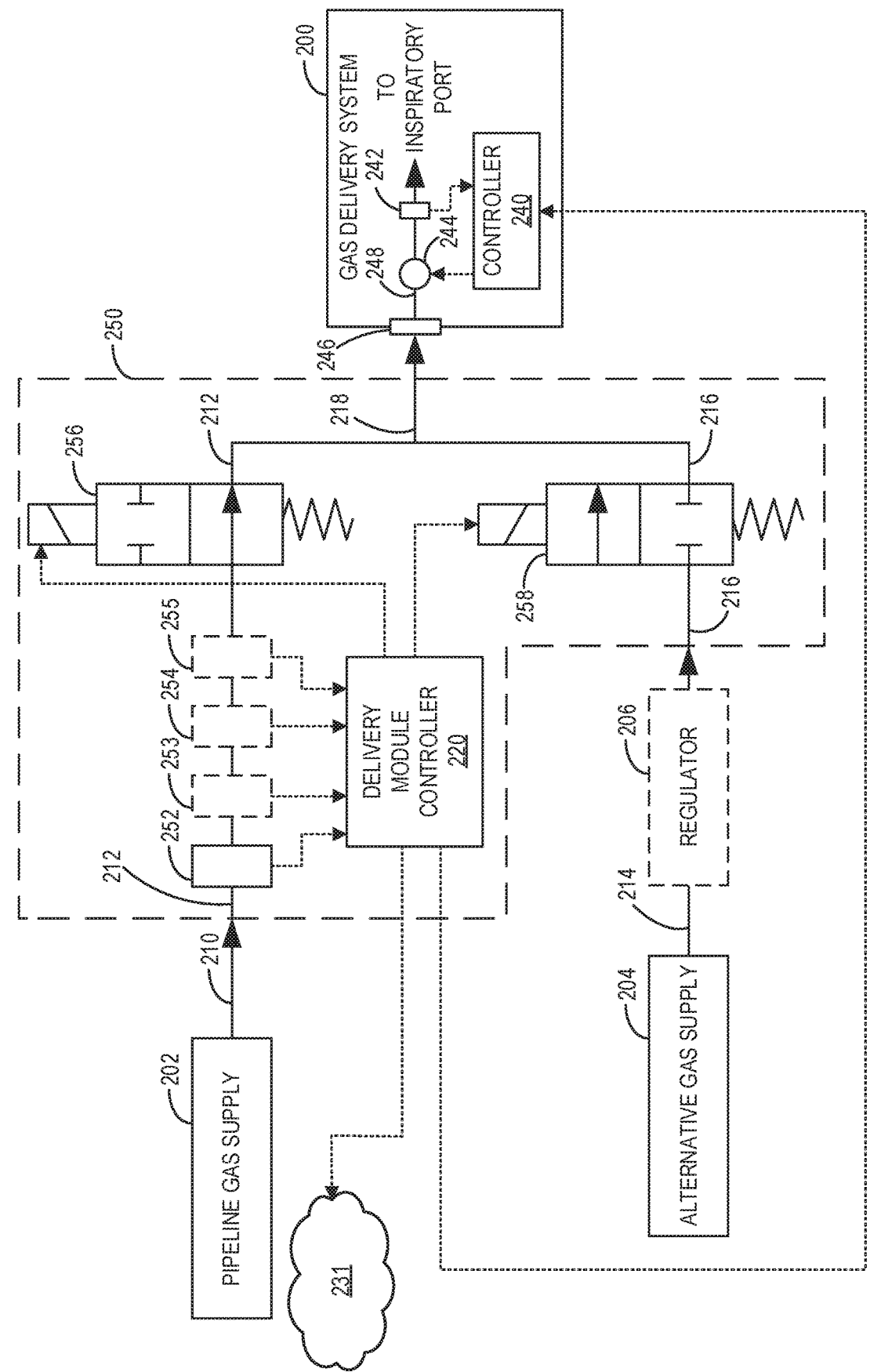
FIG. 2 schematically shows an exemplary embodiment of a medical gas delivery module configured to deliver a single medical gas to a gas delivery system.
Figure 3:
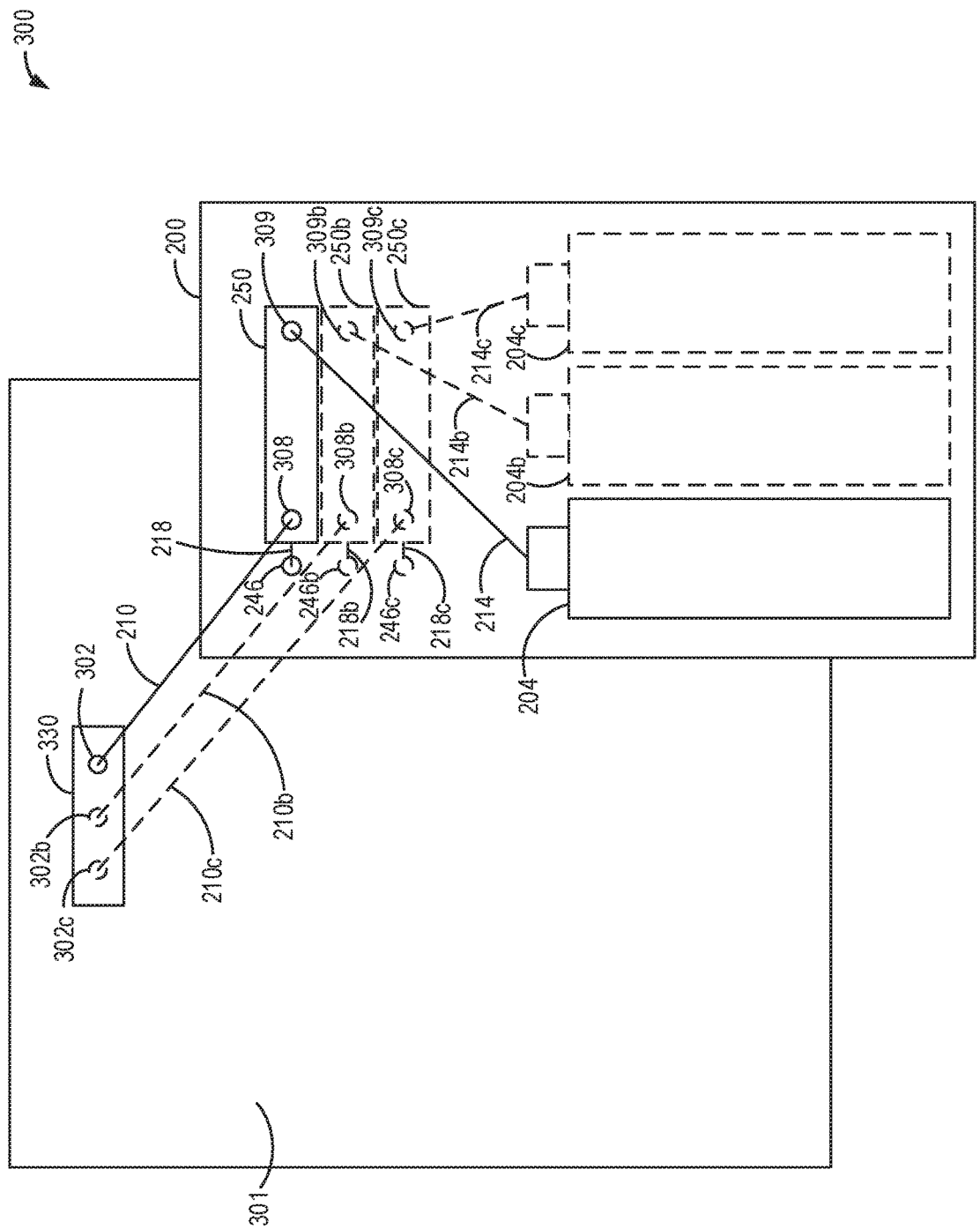
FIG. 3 schematically shows a first exemplary mounting configuration of the medical gas delivery module of FIG. 2.
Figure 4:
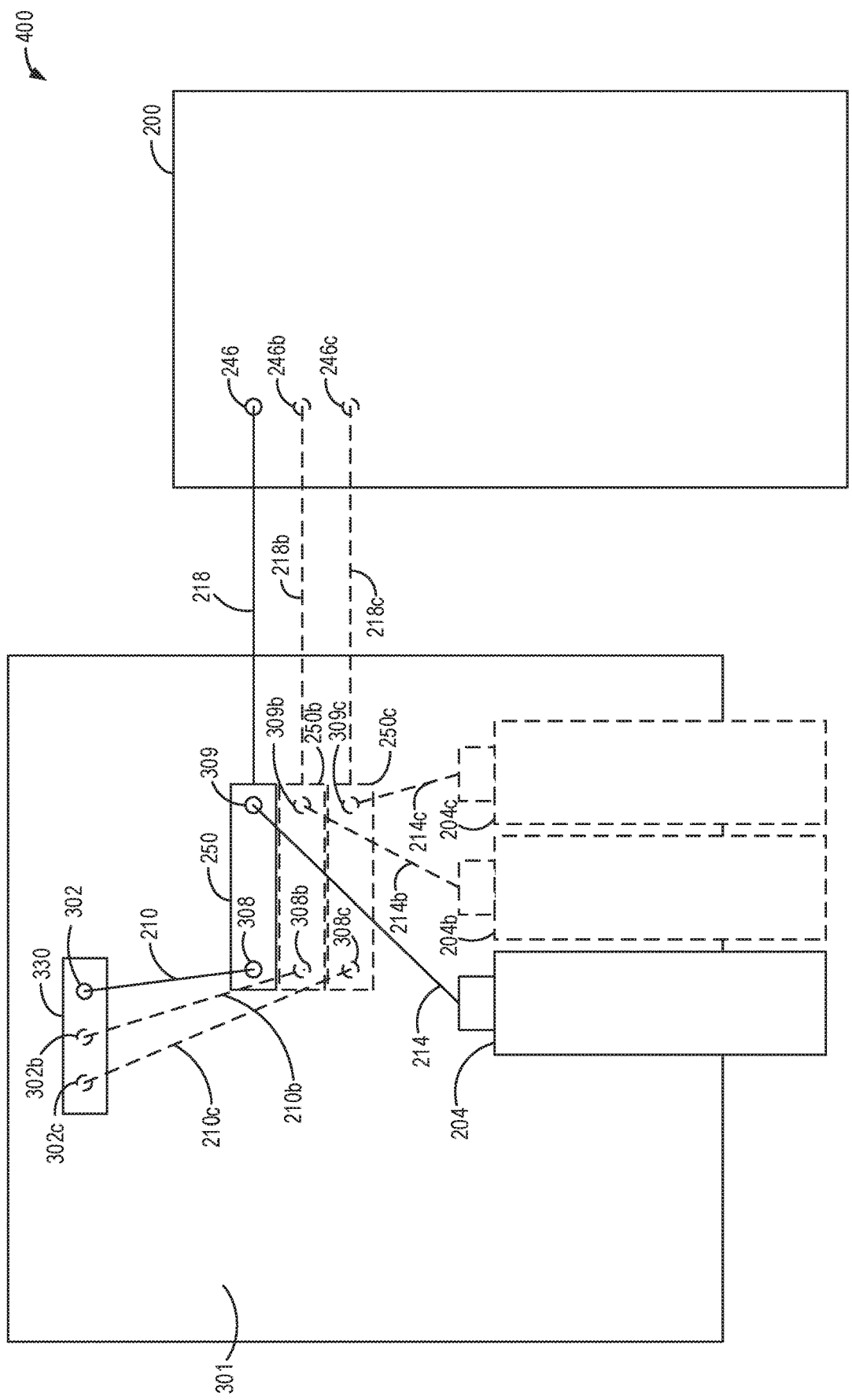
FIG. 4 schematically shows a second exemplary mounting configuration of the medical gas delivery module of FIG. 2.
Figure 5:
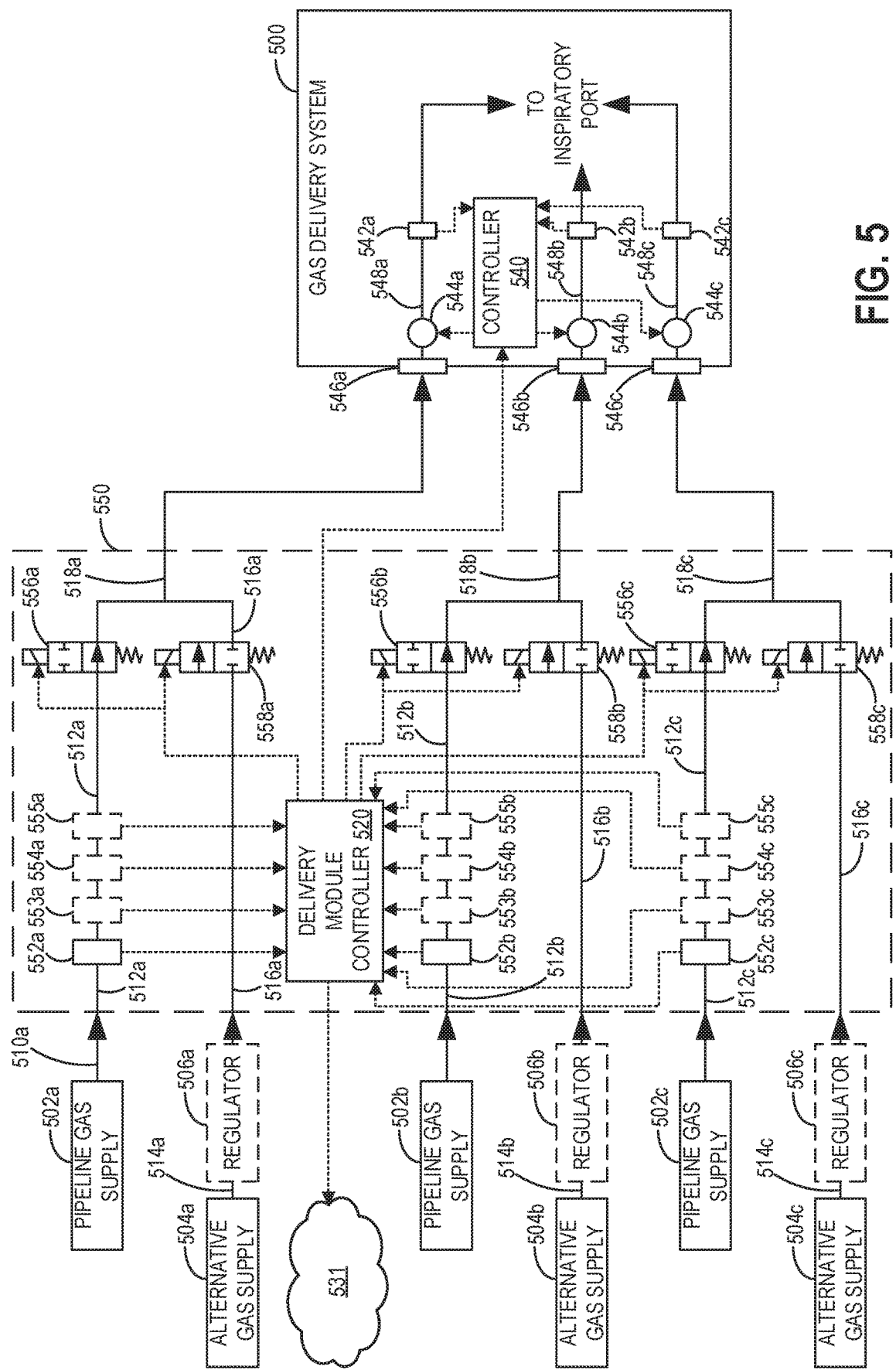
FIG. 5 schematically shows an exemplary embodiment of a medical gas delivery module configured to deliver a plurality of medical gases to a gas delivery system.
Figure 6:
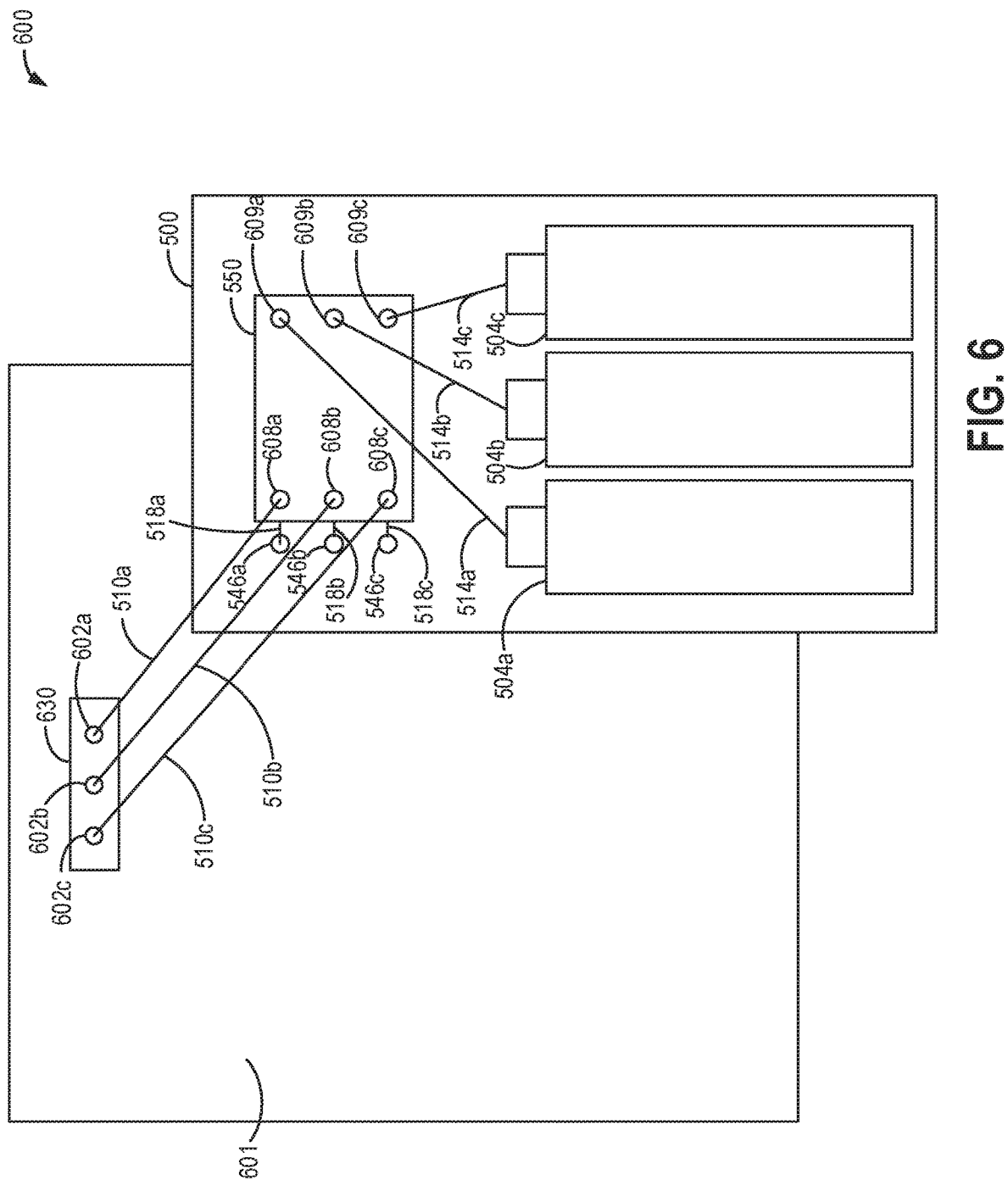
FIG. 6 schematically shows a first exemplary mounting configuration of the medical gas delivery module of FIG. 5.
Figure 7:
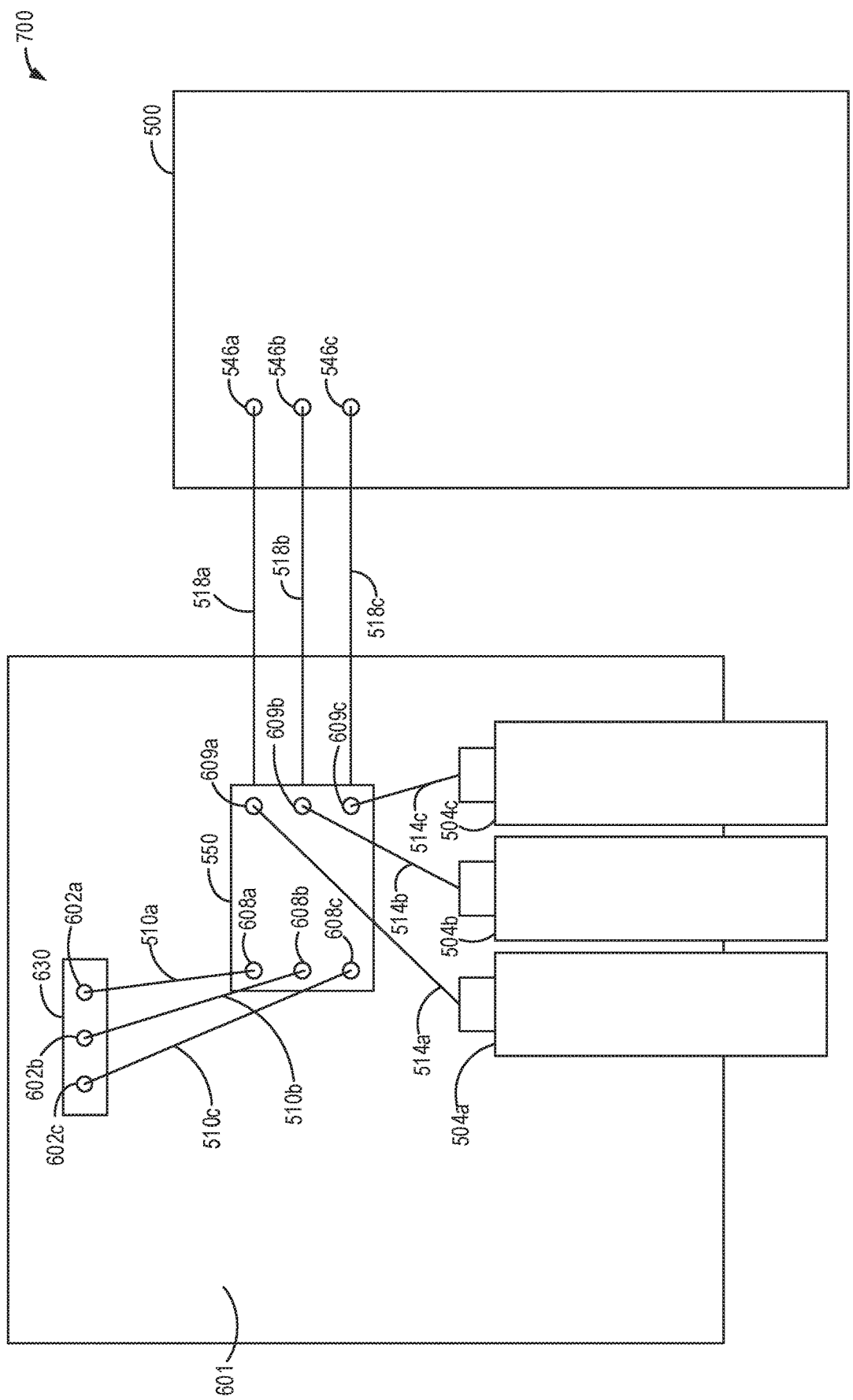
FIG. 7 schematically shows a second exemplary mounting configuration of the medical gas delivery module of FIG. 5.

FIGS. 1A-1C show views of an anesthesia machine, according to an exemplary embodiment of the invention. FIG. 2 shows a first embodiment of a medical gas delivery module, which may be configured to deliver a single medical gas to a gas delivery system, including the anesthesia machine of FIGS. 1A-1C. FIG. 5 shows a second embodiment of a medical gas delivery module, which may be configured to deliver a plurality of medical gases to a gas delivery system, including the anesthesia machine of FIGS. 1A-1C. The medical gas delivery module may be physically coupled to the gas delivery system, as shown in FIGS. 3 and 6, or may be co-located with the gas delivery system but not physically coupled to the gas delivery system, as shown in FIGS. 4 and 7. The medical gas delivery module may monitor and control gas flow to the gas delivery system according to the example method of FIG. 8. Further, a controller of the gas delivery system may adjust gas flow through the gas delivery system based on an oxygen concentration measured by the medical gas delivery module, such as according to the example method of FIG. 9.

FIGS. 1A-1C show an anesthesia machine 100 from a first side perspective view (FIG. 1A), a second side perspective view (FIG. 1B), and rear perspective view (FIG. 1C). FIGS. 1A-1C will be described collectively. Anesthesia machine 100 includes a frame 126 supported by casters 124, where the movement of the casters may be controlled (e.g., stopped) by one or more locks 7. In some examples, the frame 126 may be formed of a plastic material (e.g., polypropylene). In other examples, the frame 126 may be formed of a different type of material (e.g., metal, such as steel).

Anesthesia machine 100 also includes a respiratory gas module 1, one or more patient monitoring modules, such as a patient monitoring module 2, side rails 3, a light switch 4, an oxygen control 5, a main power indicator 6, an anesthetic agent storage bay 8, an oxygen flush button 9, a system activation switch 10 (which, in one example, permits gas flow when activated), an integrated suction 11, a ventilator 12 (explained in more detail below), an auxiliary oxygen flow control 13, an anesthetic vaporizer 14, an anesthesia display device 15, and a patient monitoring display device 16. The anesthetic vaporizer 14 may vaporize the anesthetic agent and combine the vaporized anesthetic agent with one or more medical gases (e.g., oxygen, air, nitrous oxide, nitrogen, carbon dioxide, or combinations thereof), which may then be delivered to a patient.

A rear of the anesthesia machine 100 is shown in FIG. 1C, including a gas connection panel 60. On the gas connection panel 60, one or more pipeline connectors 46 are present to facilitate coupling of the anesthesia machine to pipeline gas supply outlets 102, such as via tubing 110. For example, pipeline gas supply outlets 102 may be included in a wall mount 130, as shown in the embodiment of FIG. 1C. In other embodiments, the pipeline gas supply outlets 102 may be included in a ceiling mount, a medial hanger, a ceiling column, a bedhead unit, or other mounting locations. Each pipeline gas supply outlet 102 may provide medical gas originating from a pipeline gas supply at a central medical gas distribution system, as will be further described below. Further, although three pipeline connectors 46 and three pipeline gas supply outlets 102 are shown in the embodiment of FIG. 1C, in other embodiments, more or fewer pipeline connections and/or pipeline gas supply outlets may be included. For example, each of the pipeline gas supply outlets 102 may deliver a different type of medical gas, which may be coupled to a dedicated pipeline connector 46 for that particular type of medical gas (e.g., oxygen, air, nitrous oxide, nitrogen, or carbon dioxide). As one non-limiting illustrative example, a first pipeline gas supply outlet delivers oxygen, which is received at a first pipeline connector via a first tube; a second pipeline gas supply outlet delivers nitrous oxide, which is received at a second pipeline connector via a second tube; and a third pipeline gas supply outlet delivers medical air, which is received at a third pipeline connector via a third tube. Further still, only a subset of the pipeline connectors 46 may be coupled to a corresponding pipeline gas supply outlet 102 (e.g., via tubing 110).

Additionally, the gas connection panel 60 includes a cylinder yoke 44, via which one or more gas-holding cylinders may be coupled to the anesthesia machine. As will be further described below with respect to FIGS. 2 and 5, the gas-holding cylinders may serve as alternative gas supplies for the medical gases supplied by the pipeline gas supply outlets 102. Although two gas-holding cylinders are illustrated in the example embodiment of FIG. 1C, in other embodiments, more or fewer than two gas-holding cylinders may be included. Further, in some embodiments, an air compressor may be included in addition to or in place of one or more gas-holding cylinders. Further, as will be described below with respect to FIGS. 2-7, a medical gas delivery module may be coupled to the pipeline connectors 46 and the gas-holding cylinders in order to automatically switch from the pipeline gas supply to the gas-holding cylinder in response to an indication that the gas from the pipeline gas supply is not a desired composition.

Thus, gas may be provided to the anesthesia machine from the pipeline gas supplies and/or the gas-holding cylinders, where the gas may include but is not limited to air, oxygen, nitrogen, carbon dioxide, and nitrous oxide. The gas that enters the anesthesia machine may mix with the vaporized anesthetic agent at the anesthetic vaporizer 14, as described above, and be supplied to a patient via the ventilator 12. The rear of the anesthesia machine may also include a serial port 41, a collection bottle connection 42, a cylinder wrench storage area 43, an anesthesia gas scavenging system 45, a main power inlet 47, a system circuit breaker 48, an equipotential stud 49, an outlet circuit breaker 50, and an isolated electrical outlet 51.

As shown in FIG. 1B, the ventilator 12 may include an expiratory check valve 22 at an expiratory port, an inspiratory check valve 23 at an inspiratory port, an inspiratory flow sensor 24, an expiratory flow sensor 25, an absorber canister 26, an absorber canister release 27, a leak test plug 28, a manual bag port 29, a ventilator release 30, an adjustable pressure-limiting valve 31, a bag/vent switch 32, and a bellows assembly 33. When a patient breathing circuit is coupled to the ventilator 12, breathing gases (e.g., air, oxygen, and/or nitrous oxide mixed with vaporized anesthetic agent) exit the machine from the inspiratory port (positioned at the same location as the inspiratory check valve 23) and travel to the patient. Expiratory gases from the patient re-enter the anesthesia machine via the expiratory port (positioned at the same location as the expiratory check valve 22), where carbon dioxide may be removed from the expiratory gases via the absorber canister 26.

During operation of the anesthetic vaporizer 14, an operator (e.g., an anesthesiologist) may adjust an amount of vaporized anesthetic agent that is supplied to the patient by adjusting a flow rate of gases from the gas source(s) (e.g., the gas pipelines) to the vaporizer. The flow rate of the gases from the gas source to the vaporizer may be adjusted by the operator via adjustment of one or more flow adjustment devices. For example, the flow adjustment devices may include analog and/or digital adjustment dials and/or other user input devices configured to actuate one or more flow control valves of the anesthesia machine 100. In some embodiments, a first flow control valve may be positioned between the gas source(s) and the anesthetic vaporizer 14 and may be actuatable via the flow adjustment devices to a fully opened position, a fully closed position, and a plurality of positions between the fully opened position and the fully closed position. Various flow control valves that may be adjusted to vary the flow rate of the gases from the gas source will be further described below with respect to FIGS. 2 and 5.

The anesthesia machine may additionally include one or more valves configured to bypass gases from the gas source(s) around the anesthetic vaporizer 14. The valves may enable a first portion of gases to flow directly from the gas source to the inspiratory port and a second portion of gases to flow from the gas source through the anesthetic vaporizer 14 to mix with the vaporized anesthetic agents prior to flowing to the inspiratory port. By adjusting a ratio of the first portion of gases relative to the second portion of gases, the operator may control a concentration of vaporized anesthetic agent administered to the patient via the inspiratory port.

Further, the adjustments described above may be facilitated at least in part based on output from the respiratory gas module 1. The respiratory gas module 1 may be configured to measure various parameters of the gases exiting the vaporizer and/or being provided to the patient. For example, respiratory gas module 1 may measure the concentrations of carbon dioxide, nitrous oxide, and the anesthetic agent provided to the patient. Further, respiratory gas module 1 may measure respiration rate, minimum alveolar concentration, patient oxygen, and/or other parameters. The output from the respiratory gas module 1 may be displayed via a graphical user interface on a display device (e.g., anesthesia display device 15 and/or patient monitoring display device 16) and/or used by a controller to provide closed-loop feedback control of the amount of anesthesia provided to the patient.

Ventilator 12 may optionally be coupled to a breathing circuit (not shown) including a plurality of tubes (e.g., gas passages). The breathing circuit may be coupled between an airway of the patient (e.g., via a breathing mask positioned to enclose the mouth and/or nose of the patient, or a tracheal intubation tube) and the inspiratory port. Gases (e.g., oxygen, or a mixture of oxygen and vaporized anesthetic agents from anesthetic vaporizer 14) may flow from the inspiratory port, through the breathing circuit, and into the airway of the patient, where the gases are absorbed by the lungs of the patient. By adjusting the concentration of vaporized anesthetic agent in the gases as described above, the operator may adjust a degree to which the patient is anesthetized.

During conditions in which the breathing circuit is coupled to the airway, the anesthetic agent and/or fresh gases (without the anesthetic agent) may flow into the airway of the patient (e.g., through inhalation) via the inspiratory check valve 23. As an example, the inspiratory check valve 23 may open automatically (e.g., without input or adjustment by the operator) in response to inhalation by the patient and may close automatically in response to exhalation by the patient. Similarly, the expiratory check valve 22 may open automatically in response to exhalation by the patient and may close automatically in response to inhalation by the patient.

In some embodiments, the operator may additionally or alternatively control one or more operating parameters of the anesthesia machine 100 via an electronic controller 140 of the anesthesia machine 100. Controller 140 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. Controller 140 may be communicatively coupled (e.g., via wired or wireless connections) to one or more external or remote computing devices, such as a hospital computing system, and may be configured to send and receive various information, such as electronic medical record information, procedure information, and so forth. Controller 140 may also be electronically coupled to various other components of the anesthesia machine 100, such as the anesthetic vaporizer 14, the ventilator 12, the respiratory gas module 1, the anesthesia display device 15, and the patient monitoring display device 16.

The controller receives signals from the various sensors of the anesthesia machine 100 and employs the various actuators of the anesthesia machine 100 to adjust operation of the anesthesia machine 100 based on the received signals and instructions stored on the memory of the controller. For example, the flow of gases to the inspiratory port may be controlled via an input device (e.g., keyboard, touchscreen, etc.) coupled to the electronic controller of the anesthesia machine 100. The controller 140 may display operating parameters of the anesthesia machine 100 via anesthesia display device 15 and/or patient monitoring display device 16. The controller may receive signals (e.g., electrical signals) via the input device and may adjust operating parameters of the anesthesia machine 100 in response (e.g., responsive) to the received signals.

As one example, the operator may input a desired concentration of the anesthetic agent to be delivered to the patient. A corresponding valve position of one or more valves of the anesthesia machine (e.g., a position of one or more flow control valves and/or bypass valves, as described above) may be empirically determined and stored in a predetermined lookup table or function in a memory of the controller. For example, the controller may receive the desired concentration of the anesthetic agent via the input device and may determine an amount of opening of the one or more valves corresponding to the desired concentration of the anesthetic agent based on the lookup table, with the input being the concentration of the anesthetic agent and the output being the valve position of the one or more valves. The controller may transmit an electrical signal to an actuator of the one or more valves in order to adjust each of the one or more valves to the corresponding output valve position. In some examples, the controller may compare the desired flow rate of gases to a measured flow rate of gases, such as measured by inspiratory flow sensor 24, for example.

Controller 140 is shown in FIGS. 1A and 1C for illustrative purposes, and it is to be understood that controller 140 may be located internally of anesthesia machine 100 and thus may not be visible externally on anesthesia machine 100. Additionally, controller 140 may include multiple devices/modules that may be distributed throughout anesthesia machine 100. As such, controller 140 may include a plurality of controllers at various locations within anesthesia machine 100 and/or external to anesthesia machine 100 that are communicatively coupled through wired and/or wireless connections.

As mentioned above, gas delivered to anesthesia machine 100 via pipeline gas supply outlets 102 may originate at a central medical gas distribution system. The central medical gas distribution system may be located in a same facility (e.g., a healthcare facility) as anesthesia machine 100 but in a different area of the facility, for example. Therefore, the pipeline gas supply may provide anesthesia machine 100 with medical gas from a remote location within the facility. For example, a pipeline network may carry the medical gas from the central medical gas distribution system to the pipeline gas supply outlets 102, which may serve as a terminal outlet for the medical gas at a point of use (e.g., at an operating theater, a ward, a patient room, etc.). In one embodiment, the pipeline network is comprised of copper pipes. Each pipeline gas supply outlet 102 may be color-coded based on the medical gas delivered and labeled with the medical gas name. Further, each pipeline gas supply outlet 102 may include self-sealing sockets that accept a gas-specific plug to couple the tubing 110 to the pipeline gas supply outlet 102, and thus to pipeline connector 46 of anesthesia machine 100.

The central medical gas distribution system may include various equipment, including but not limited to gas-holding cylinders and/or tanks, gas manifolds (e.g., coupled to the gas-holding cylinders and/or tanks), air compressors, vacuum pumps, generators, and concentrators. For example, some types of medical gas, such as nitrogen, nitrous oxide, and carbon dioxide, may be purchased from an outside supplier in pre-filled cylinders. The pre-filled cylinders may be coupled to a manifold that automatically switches from an empty cylinder to a full cylinder (e.g., in response to a pressure of the cylinder decreasing below a threshold pressure that indicates that the cylinder is empty) in order to supply a constant stream of gas. Thus, the pipeline gas supply for such gases may include the pre-filled cylinders, the manifold, and the piping network coupled to the manifold, as well as various valves (e.g., shut-off valves), filters, sensors, and the pipeline gas supply outlet. Other types of medical gas, such as air, may be generated on-site by the central medical gas distribution system. For example, ambient air may be compressed by an air compressor of the central medical gas distribution system, dried via an air dryer, and stored in air tanks and/or cylinders (e.g., via a filling system). Thus, in such an example, the pipeline gas supply may also include the air compressor and the air dryer.

In some embodiments, oxygen may be generated on-site. For example, a portion of the compressed and dried air (which is approximately 78% nitrogen, 21% oxygen, and 1% argon and other gases) may be distributed to an oxygen generator that separates the oxygen component of the air from the other components. The oxygen may be concentrated via an oxygen concentrator to produce gas that is approximately 92-93% oxygen (e.g., greater than 90% oxygen). Thus, the pipeline gas supply for oxygen generated via an oxygen concentrator may further include the oxygen generator and the oxygen concentrator. In other embodiments, oxygen may be purchased from an outside supplier in pre-filled cylinders and/or tanks instead of generated on-site. In such an embodiment, the gas in the pre-filled cylinders and/or tanks may be approximately 100% oxygen.

Thus, the central medical gas distribution system may include a pipeline gas supply for each of the various medical gases, each pipeline gas supply including equipment for storing, distributing, and in some examples generating the corresponding medical gas. In particular, the gases generated on-site (e.g., air and optionally oxygen) may be exposed to more potential sources of contamination compared with gases sourced from pre-filled cylinders and/or tanks. For example, water is a common contaminant of medical air that may be introduced via inadequate drying via the air dryers (such as from using an undersized dryer or due to dryer saturation, for example), via degraded air compressor components, or degradation of other central medical gas distribution system components. Oil, another potential contaminant, may be introduced via the compressor, such as when a non-medical grade compressor is used or compressor degradation occurs. Further, particulate debris may be introduced to the pipeline network from sand, dirt, solder, flux, etc.

While the central medical gas distribution system may include various monitors for detecting medical gas contamination and alarms for alerting localized, central medical gas distribution system personnel of the contamination, the alarms may be limited to the central medical gas distribution system location. Further, the alarms may not actively prevent further delivery of the contaminated gas to downstream equipment, such as anesthesia machine 100. For example, the operator of anesthesia machine 100 may be unaware of the alarms at the central medical gas distribution system location and may continue to operate the anesthesia machine with the contaminated gas. As a result, the contaminated gas may degrade components of anesthesia machine 100 and may be supplied to the patient.

In some embodiments, anesthesia machine diagnostic routines, such as performed by controller 140, may detect the degradation resulting from the contaminated gas supply and shut down the machine. However, the source of the degradation may remain unknown. For example, the controller may make a determination that degradation is present (such as degradation of one or more valves and sensors of the anesthesia machine, which may be sensitive to moisture, oil, and particulate matter), and in response to the determination of degradation, shut down and/or prevent operation of anesthesia machine 100. Further, the controller may log the degradation (e.g., in an error log). However, the controller may not provide any information about the source of the degradation, only that the degradation is present. Therefore, the contaminated gas may continue to be supplied to additional medical gas delivery systems (e.g., anesthesia machines and/or ventilators), spreading the contamination and degradation. Gas delivery system degradation and shutdown may lead to user frustration and result in high repair costs, particularly when multiple gas delivery systems of the facility are affected.

Further, gas that is not of the expected composition may be supplied from the central medical gas distribution system. For example, a cylinder containing nitrogen gas may be coupled to an oxygen gas manifold instead of a cylinder containing oxygen gas, resulting in nitrogen gas being supplied from the oxygen pipeline gas supply and an incorrect composition of gas being delivered to the patient.

Therefore, FIG. 2 shows a first exemplary embodiment of a medical gas delivery module 250, which may be used to selectively supply gas from a pipeline gas supply 202 to a gas delivery system 200. In one embodiment, pipeline gas supply 202 includes pipeline gas supply outlet 102 shown in FIG. 1C, and gas delivery system 200 is anesthesia machine 100 of FIGS. 1A-1C. Pipeline gas supply 202 may further include one or more pre-filled cylinders, manifolds, pipes, valves, filters, sensors, compressors, dryers, and/or concentrators depending on the particular medical gas supplied by pipeline gas supply 202, as described above. The medical gas from pipeline gas supply 202 may flow to medical gas delivery module 250 via a conduit 210, which may be flexible tubing, for example (e.g., tubing 110 shown in FIG. 1C). Conduit 210 may be coupled to a housing of medical gas delivery module 250 via a connector, for example, to fluidly couple medical gas delivery module 250 to pipeline gas supply 202. The medical gas from pipeline gas supply 202 flows within medical gas delivery module 250 via a conduit 212, which may be comprised of a same or different material as conduit 210. In one embodiment, conduit 212 is comprised of metal piping, such as steel, copper, or brass piping. The connector may couple conduit 210 to conduit 212, forming a gas-tight seal between conduit 210 and conduit 212 so that medical gas flows from pipeline gas supply 202 into medical gas delivery module 250 without escaping to atmosphere.

A valve 256 coupled to conduit 212 may be used to selectively block gas flow through conduit 212. For example, valve 256 may be a 2/2-way solenoid actuated valve with a spring return, as shown in FIG. 2, that may be switched between a fully open and a fully closed position based on whether or not the solenoid is energized (e.g., activated). A delivery module controller 220 may adjust operation of valve 256, and thereby medical gas delivery module 250, in response to one or more electronic feedback signals received by delivery module controller 220, as will be further described below. In one example embodiment, as shown in FIG. 2, valve 256 is a normally open valve that is opened when de-energized (e.g., deactivated) by delivery module controller 220 and closed when energized (e.g., activated).

A gas quality sensor 252 is positioned within conduit 212 upstream of valve 256 to measure a quality of the medical gas delivered from pipeline gas supply 202. For example, gas quality sensor 252 may provide the electronic feedback signal to delivery module controller 220 for operating valve 256. The quality may be any gas quality of interest, such as humidity (e.g., where gas quality sensor 252 is a humidity sensor), hydrocarbon concentration (e.g., where gas quality sensor 252 is a hydrocarbon sensor), particulate concentration (e.g., where gas quality sensor 252 is a particulate matter sensor), or gas composition (e.g., where gas quality sensor 252 is an oxygen sensor), although other measurable gas qualities are also possible. Additional gas quality sensors 253, 254, 255 may be optionally included in medical gas delivery module 250 and coupled to conduit 212. For example, each of gas quality sensor 252, gas quality sensor 253, gas quality sensor 254, and gas quality sensor 255 may measure one gas quality of interest. In some embodiments, a subset of the optional gas quality sensors 253, 254, 255 are coupled to conduit 212. In other embodiments, all of the optional gas quality sensors 253, 254, 255 are coupled to conduit 212. In still other embodiments, more than four gas quality sensors are coupled to conduit 212.

The number of gas quality sensors included in medical gas delivery module 250 and the qualities measured by the included gas quality sensors may vary based on the type of medical gas delivered by the pipeline gas supply 202. As one exemplary embodiment, when the medical gas is air, gas quality sensor 252 may be included as a humidity sensor, gas quality sensor 253 may be included as a hydrocarbon sensor, gas quality sensor 254 may be included as a particulate matter sensor, and gas quality sensor 255 may be included as an oxygen sensor to ensure that the air supplied to gas delivery system 200 via medical gas delivery module 250 is clean, dry, and of an expected composition. For example, the humidity sensor, configured to detect water vapor, may output a signal to delivery module controller 220 indicating an amount (or dew point) of water vapor in the air supplied from pipeline gas supply 202; the hydrocarbon sensor, configured to detect hydrocarbons (including grease and oil), may output a signal to delivery module controller 220 indicating an amount (or concentration) of hydrocarbons in the air supplied from pipeline gas supply 202; the particulate matter sensor, configured to detect organic and inorganic particles suspended in the air, may output a signal to delivery module controller 220 indicating an amount (or concentration) of particulate matter in the air supplied from pipeline gas supply 202; and the oxygen sensor may output a signal to delivery module controller 220 indicating an amount (or concentration) of oxygen in the air supplied from pipeline gas supply 202.

For example, medical air is often generated via a compressor and gas drying system, as described above. Insufficient gas drying, which may result in water vapor in the air, may be detected via the humidity sensor. As one example, the humidity sensor may be configured to measure both a temperature and a moisture (e.g., water vapor) content of the air supplied from pipeline gas supply 202 to determine a relative humidity of the air (e.g., a ratio of the measured moisture in the air to the maximum possible amount of moisture at the measured temperature, which may be expressed as a percentage). Further, air is approximately 21% oxygen. The measurement made by the oxygen sensor may be used to distinguish air from gases with other oxygen concentrations, such as when the oxygen sensor measures approximately 0% oxygen (e.g., when nitrogen is supplied instead of air) or approximately 100% oxygen (e.g., when oxygen is supplied instead of air). The hydrocarbon sensor may indicate contamination by oil, such as oil from the compressor or delivery pipes, and the particulate matter sensor may indicate particulate contamination, such as where the air is not sufficiently filtered and/or is contaminated downstream of the filters. Water vapor, oil, bacterial growth, and particulate contamination of the air may degrade components of gas delivery system 200, for example. Further, delivery of a clean, correct medical gas to a patient via the gas delivery system 200 is desired. Therefore, in response to any of the measured qualities being outside of a corresponding allowable range, delivery module controller 220 may close valve 256 to prevent air from pipeline gas supply 202 from flowing to gas delivery system 200, as will be further described below with respect to FIG. 8.

Other combinations of gas quality sensors may be used when different gases are supplied by pipeline gas supply 202 based on the type of gas supplied and the gas source. As another exemplary embodiment, when the medical gas is nitrogen sourced from pre-filled cylinders located at the central medical gas distribution system, there are fewer potential sources of contamination. Therefore, gas quality sensor 252 may be included as an oxygen sensor to detect deviations from the expected gas composition (e.g., approximately 0% oxygen when nitrogen gas is delivered), and one or more or all of the optional gas quality sensors 253, 254, and 255 may be omitted. For example, in response to receiving a signal from gas quality sensor 252 corresponding to approximately 100% oxygen, indicating that oxygen and not nitrogen is being delivered, delivery module controller 220 may close valve 256. Similarly, in exemplary embodiments where the medical gas is oxygen sourced from pre-filled cylinders located at the central medical gas distribution system, gas quality sensor 252 may be included as an oxygen sensor to detect deviations from the expected gas composition (e.g., approximately 100% oxygen). Further, in exemplary embodiments where the medical gas is oxygen sourced from an oxygen concentrator located at the central medical gas distribution system, delivery module controller 220 may not only confirm the gas composition via the oxygen sensor (e.g., around 93% oxygen), but may transmit the measured oxygen concentration to a controller 240 of gas delivery system 200, as will be further described below.

Further, in response to any of the measured gas qualities being outside of the corresponding allowable range, delivery module controller 220 may open a valve 258 disposed within a conduit 216 that is configured to flow medical gas received from an alternative gas supply 204. Alternative gas supply 204 may be fluidly coupled to medical gas delivery module 250 via a conduit 214. Conduit 214 may be coupled to the housing of medical gas delivery module 250 via a connector, for example, forming a gas-tight seal between conduit 214 and conduit 216. Conduit 214 may be comprised of flexible tubing similar to conduit 210, for example. Alternatively, conduit 214 may be comprised of a rigid material, such as metal. Similarly, conduit 216 may be comprised of a same or different material as conduit 212. In some embodiments, alternative gas supply 204 is a gas-holding cylinder storing a same gas as desired from pipeline gas supply 202. In other embodiments, alternative gas supply 204 is a compressor, such as where the desired gas from pipeline gas supply 202 is air. Further, in some embodiments, a regulator 206 may be disposed in conduit 214 between alternative gas supply 204 and medical gas delivery module 250 to control a pressure of gas supplied from alternative gas supply 204 to medical gas delivery module 250.

Valve 258 coupled to conduit 216 may be used to selectively enable or block gas flow through conduit 216. For example, valve 258 may be a 2/2-way solenoid actuated valve with a spring return, as illustrated in FIG. 2. Delivery module controller 220 may adjust operation of valve 258, and thereby medical gas delivery module 250, in response to the one or more electronic feedback signals received by delivery module controller 220 from gas quality sensor 252 and any of the optional gas quality sensors 253, 254, and 255 disposed in conduit 212. In one exemplary embodiment, as shown in FIG. 2, valve 258 is a normally closed valve that is opened when energized by delivery module controller 220 and closed when de-energized. In another exemplary embodiment, valve 258 is a normally open valve that is closed when energized by delivery module controller 220 and open when de-energized.

Delivery module controller 220 may maintain valve 258 closed while valve 256 is open and open valve 258 in response to closing valve 256. For example, delivery module controller 220 may simultaneously close valve 256 and open valve 258 in response to one or more measured gas qualities being outside of the corresponding allowable range, as will be further described below with respect to FIG. 8. In this way, through coordinated valve control, only one of valve 256 and valve 258 may be open at a given time.

Gas from either pipeline gas supply 202 or alternative gas supply 204 may exit medical gas delivery module 250 via a conduit 218, which may fluidly couple medical gas delivery module 250 to gas delivery system 200. For example, conduit 218 may be coupled to gas delivery system 200 via a pipeline connector 246 (which may be pipeline connector 46 shown in FIG. 1C, for example). Conduit 212 is coupled to conduit 218 downstream of valve 256, and conduit 216 is coupled to conduit 218 downstream of valve 258. For example, as shown in FIG. 2, conduit 212, conduit 216, and conduit 218 may meet at a three-way junction. As an example, when valve 256 is open (and valve 258 is closed), gas from pipeline gas supply 202 may flow through conduit 212 into conduit 218 and may be received by gas delivery system 200 via conduit 218. Conversely, when valve 258 is open (and valve 256 is closed), gas from alternative gas supply 204 may flow through conduit 216 into conduit 218 and may be received by gas delivery system 200 via conduit 218. Gas received via conduit 218 may flow through gas delivery system 200 toward an inspiratory port via a conduit 248. Conduit 248 includes a flow control valve 244 and a flow sensor 242 disposed therein. For example, flow control valve 244 may be a proportional valve that may be adjusted by controller 240 to a plurality of positions between open (e.g., fully open) and closed (e.g., fully closed), thereby varying a flow rate of gas downstream of flow control valve 244. For example, controller 240 may adjust flow control valve 244 based on a flow rate (e.g., mass flow rate) measured by flow sensor 242, positioned downstream of flow control valve 244, to achieve a target flow setpoint downstream of flow control valve 244, as will be further described below with respect to FIG. 9.

In some embodiments, such as where gas delivery system 200 is an anesthesia machine, at least a portion of the gas may first flow through an anesthetic vaporizer (e.g., anesthetic vaporizer 14 described with reference to FIG. 1A) prior to flowing to the inspiratory port and to the patient (e.g., via a patient breathing circuit). Therefore, while only one conduit 248 is shown, additional conduits, chambers, etc. may be included between pipeline connector 246 and the inspiratory port. Similarly, additional flow control valves and sensors may be coupled in a flow path between pipeline connector 246 and the inspiratory port.

In addition to actuating valve 256 and valve 258 in response to any of the measured gas qualities being outside of the corresponding allowable range, delivery module controller 220 may further communicate a pipeline gas supply error message to the gas delivery system controller 240 as well as well as to a remote error log, such as stored on a remote network 231, as will be further described below with respect to FIG. 8. For example, delivery module controller 220 may be communicatively coupled to gas delivery system controller 240 and remote network 231 via wired or wireless connections (such as Bluetooth, Wi-Fi, etc.). In one embodiment, remote network 231 is included in a Cloud computing network. Remote network 231 may enable a manufacturer of medical gas delivery module 250 and/or gas delivery system 200 to access the remote error log, such as for performance monitoring and maintenance. For example, after a pipeline gas supply error is detected by medical gas delivery module 250, medical gas delivery module 250 may be serviced by the manufacturer to clean or replace contaminated components (e.g., gas quality sensors, valves, and/or conduits), such as where hydrocarbon, water vapor, and/or particulate matter contamination is detected. Further, although the medical gas delivery module 250 limits the exposure of gas delivery system 200 to contaminated gas, in some examples, gas delivery system 200 also may be serviced to prevent and/or reduce valve and sensor degradation. In this way, an occurrence of gas delivery system 200 degradation and shutdown may be reduced.

Further, when the gas supplied by pipeline gas supply 202 is oxygen sourced from an oxygen concentrator and gas quality sensor 252 is an oxygen sensor, delivery module controller 220 may transmit the oxygen concentration measured by gas quality sensor 252 to controller 240 in response to the measured oxygen concentration being within the corresponding allowable range. As will be further described below with respect to FIGS. 8 and 9, controller 240 may adjust a flow setpoint for the oxygen sourced from the oxygen concentrator based on the measured oxygen concentration.

Medical gas delivery module 250 may be coupled in various locations at a point of use. Turning briefly to FIGS. 3 and 4, schematic views of different mounting locations of medical gas delivery module 250 are shown. FIG. 3 shows a first schematic view 300, and FIG. 4 shows a second schematic view 400. Like components of FIGS. 2-4 are numbered the same and may not be reintroduced.

In each of views 300 and 400, medical gas delivery module 250 is shown receiving gas from a pipeline gas supply outlet 302 (which may be one of the pipeline gas supply outlets 102 shown in FIG. 1C, for example) included in a wall mount 330, mounted on a wall 301, via conduit 210. Conduit 210 couples to medical gas delivery module 250 via a connector 308. Similarly, medical gas delivery module 250 is shown receiving gas from alternative gas supply 204 via conduit 214, which is coupled to medical gas delivery module 250 via a connector 309.

In some embodiments, a plurality of medical gas delivery modules may be included for delivering a plurality of medical gases. For example, views 300 and 400 optionally show a second medical gas delivery module 250b and a third medical gas delivery module 250c coupled to gas delivery system 200, although more than three or fewer than three medical gas delivery modules may be included (e.g., two). For example, second medical gas delivery module 250b may receive a second medical gas from a second pipeline gas supply outlet 302b via a conduit 210b that is coupled to second medical gas delivery module 250b via a connector 308b. Second medical gas delivery module 250b may also receive the second medical gas from an alternative gas supply 204b via a conduit 214b that is coupled to second medical gas delivery module 250b via a connector 309b. Second medical gas delivery module 250b may output the second medical gas to gas delivery system 200 via a conduit 218b coupled to gas delivery system 200 via a connector 246b. Similarly, third medical gas delivery module 250c may receive a third medical gas from a third pipeline gas supply outlet 302c via a conduit 210c that is coupled to third medical gas delivery module 250c via a connector 308c. Third medical gas delivery module 250c may also receive the third medical gas from an alternative gas supply 204c via a conduit 214c that is coupled to second medical gas delivery module 250c via a connector 309c. Third medical gas delivery module 250c may output the second medical gas to gas delivery system 200 via a conduit 218c coupled to gas delivery system 200 via a connector 246c.

In some embodiments, medical gas delivery module 250, second medical gas delivery module 250b, and third medical gas delivery module 250c may be individual systems each including their own controller (e.g., delivery module controller 220) and the other components described with respect to FIG. 2. For example, each of medical gas delivery module 250, second medical gas delivery module 250b, and third medical gas delivery module 250c may be configured to deliver one particular medical gas and include the corresponding hardware (e.g., relevant gas quality sensors) and software (e.g., instructions included in the memory of the delivery module controller) for delivering that particular medical gas to gas delivery system 200. Thus, an operator of gas delivery system 200 may select the appropriate medical gas delivery module (or modules) to be used with gas delivery system 200 for delivering a desired medical gas (or gases).

In the embodiment shown in FIG. 3, medical gas delivery module 250 (and the optional second medical gas delivery module 250b and third medical gas delivery module 250c) is physically coupled to gas delivery system 200. For example, a housing of medical gas delivery module 250 may be mounted to gas delivery system 200, directly or indirectly, via screws, brackets, or other appropriate fasteners such that medical gas delivery module 250 is integrated into gas delivery system 200. In other embodiments, medical gas delivery module 250 (and the optional second medical gas delivery module 250b and third medical gas delivery module 250c) may not be physically coupled to gas delivery system 200. For example, in the embodiment illustrated in FIG. 4, medical gas delivery module 250 (and the optional second medical gas delivery module 250b and third medical gas delivery module 250c) is physically coupled to wall 301, such as via mounting screws, brackets, or any other appropriate fasteners. In still other embodiments, medical gas delivery module 250 (and the optional second medical gas delivery module 250b and third medical gas delivery module 250c) may be a standalone system that is not physically coupled to either of gas delivery system 200 or wall 301.

Returning to FIG. 2, delivery module controller 220 includes a processor operatively connected to a memory. The memory may be a non-transitory computer-readable medium and may be configured to store computer executable code (e.g., instructions) to be processed by the processor in order to execute one or more routines, such as those described herein. The memory may also be configured to store data received by the processor. For example, delivery module controller 220 may be configured as a conventional microcomputer, including a microprocessor unit, input/output ports, read-only memory, random access memory, keep alive memory, a controller area network (CAN) bus, etc. Delivery module controller 220 may receive input data from the various sensors (e.g., gas quality sensor 252), process the input data, and trigger the actuators (e.g., valve 256 and valve 258) in response to the processed input data based on instruction or code programmed therein corresponding to one or more routines, an example of which is described below with reference to FIG. 8.

Similarly, controller 240 of gas delivery system 200 also may be configured as a conventional microcomputer, including a microprocessor unit, input/output ports, read-only memory, random access memory, keep alive memory, a controller area network (CAN) bus, etc. Controller 240 may receive input data from the various sensors (e.g., flow sensor 242) as well as from delivery module controller 220, process the input data, and trigger the actuators (e.g., flow control valve 244) in response to the processed input data based on instruction or code programmed therein corresponding to one or more routines, an example of which is described below with reference to FIG. 9.

In this way, the system of FIG. 2 provides for an uninterrupted delivery of a desired medical gas to a gas delivery system (e.g., an anesthesia machine and/or ventilator) via a medical gas delivery module and ensures that the medical gas delivered is uncontaminated and of a desired composition. The medical gas delivery module, including a controller, one or more gas quality sensors, and controller-actuated valves, may automatically switch to an alternative gas supply in response to detected contamination and/or compositional deviations in gas provided by a pipeline gas supply without user intervention. Further, the medical gas delivery module may alert a user of the gas delivery system that the pipeline gas supply is delivering gas of an undesired composition (e.g., due to contamination or a different gas being supplied).

Next, FIG. 5 shows a second exemplary embodiment of a medical gas delivery module 550. Whereas medical gas delivery module 250 shown in FIG. 2 is configured to provide a single medical gas to a gas delivery system, medical gas delivery module 550 is configured to provide a plurality of medical gases to a gas delivery system 500. Like components of FIGS. 2 and 5 are numbered similarly (e.g., gas delivery system 200 corresponds to gas delivery system 500) and function as described with respect to FIG. 2, and therefore may not be reintroduced. Further, letters (e.g., "a," "b," and "c") designate a set of components involved in delivering one of the plurality of medical gases to gas delivery system 500. That is, the "a" components (e.g., conduit 512a) deliver a first medical gas (from pipeline gas supply 502a or alternative gas supply 504a) to gas delivery system 500, the "b" components (e.g., conduit 512b) deliver a second medical gas (from pipeline gas supply 502b or alternative gas supply 504b) to gas delivery system 500, and the "c" components (e.g., conduit 512c) deliver a third medical gas (from pipeline gas supply 502c or alternative gas supply 504c) to gas delivery system 500. Although three sets of components (e.g., "a," "b," and "c") are shown in the exemplary embodiment of FIG. 5 for delivering three medical gases, in other embodiments, more than three sets of components or fewer than three sets of components (e.g., two) may be included in medical gas delivery module 550 and gas delivery system 500. Therefore, the embodiment shown in FIG. 2 provides for a single gas delivery module, and the embodiment shown in FIG. 5 provides for a multi-gas delivery module.

Controller 520 may simultaneously monitor and control the delivery of medical gas from pipeline gas supply 502a, pipeline gas supply 502b, and pipeline gas supply 502c to gas delivery system 500. Further, the supply of each of the plurality of medical gases is controlled individually such that a pipeline gas supply error for one of the medical gases does not affect the delivery of the other gases. For example, controller 520 may adjust operation of valves 556a and 558a based on electronic feedback signals received from gas quality sensor 552a and optional gas quality sensors 553a, 554a, and 555a (and not from any of the gas quality sensors 552b, 553b, 554b, 555b, 552c, 553c, 554c, and 555c); adjust operation of valves 556b and 558b based on electronic feedback signals received from gas quality sensor 552b and optional gas quality sensors 553b, 554b, and 555b (and not from any of the gas quality sensors 552a, 553a, 554a, 555a, 552c, 553c, 554c, and 555c); and adjust operation of valves 556c and 558c based on electronic feedback signals received from gas quality sensor 552c and optional gas quality sensors 553c, 554c, and 555c (and not from any of the gas quality sensors 552a, 553a, 554a, 555a, 552b, 553b, 554b, and 555b). As an illustrative example, in response to the gas quality measured by gas quality sensor 552a being outside of the corresponding allowable range while the gas qualities measured by gas quality sensor 552b and 552c remain within their corresponding allowable ranges, controller 520 may close valve 556a while opening valve 558a to switch from pipeline gas supply 502a to alternative gas supply 504a for supplying the first medical gas. At the same time, controller 520 may maintain valve 556b open and valve 558b closed to continue supplying the second medical gas from pipeline gas supply 502b (and not from alternative gas supply 504b) and maintain valve 556c open and valve 558c closed to continue supplying the third medical gas from pipeline gas supply 502c (and not from alternative gas supply 504c).

Controller 540 of gas delivery system 500 may actuate flow control valves 544a, 544b, and 544c individually or in combination to achieve a desired mixture of each of the plurality of gases downstream at the inspiratory port. For example, controller 540 may decrease an opening of valve 544a to decrease a flow rate of the first medical gas through conduit 548a, downstream of flow control valve 544a, and increase an opening of valve 544b to increase a flow rate of the second medical gas through conduit 548b, downstream of flow control valve 544b, based on feedback signals received from flow sensors 542a and 542b, respectively, and the desired mixture.

Similar to medical gas delivery module 250 of FIG. 2, medical gas delivery module 550 of FIG. 5 may be coupled in various locations at a point of use. FIGS. 6 and 7 show schematic views of different mounting locations of medical gas delivery module 550. FIG. 6 shows a first schematic view 600, and FIG. 7 shows a second schematic view 700. Like components of FIGS. 5-7 are numbered the same and may not be reintroduced.

In each of views 700 and 600, multi-medical gas delivery module 550 is shown receiving gas from pipeline gas supply outlets 602a, 602b, and 602c (which may be pipeline gas supply outlets 102 shown in FIG. 1C, for example) included in a wall mount 630, mounted on a wall 601, via conduits 510a, 510b, and 510c, respectively. Conduit 510a couples to medical gas delivery module 550 via a connector 608a, conduit 510b couples to medical gas delivery module 550 via a connector 608b, and conduit 510c couples to medical gas delivery module 550 via a connector 608c. Similarly, medical gas delivery module 550 is shown receiving gas from alternative gas supply 504a via conduit 514a, which is coupled to medical gas delivery module 550 via a connector 609a, from alternative gas supply 504b via conduit 514b, which is coupled to medical gas delivery module 550 via a connector 609b, and from alternative gas supply 504c via conduit 514c, which is coupled to medical gas delivery module 550 via a connector 609c.

In the embodiment shown in FIG. 6, medical gas delivery module 550 is physically coupled to gas delivery system 500. For example, a housing of medical gas delivery module 550 may be mounted to gas delivery system 500, directly or indirectly, via screws, brackets, or other appropriate fasteners such that medical gas delivery module 550 is integrated into gas delivery system 500. In other embodiments, medical gas delivery module 550 may not be physically coupled to gas delivery system 500. For example, in the embodiment illustrated in FIG. 7, medical gas delivery module 550 is physically coupled to wall 601, such as via mounting screws, brackets, or any other appropriate fasteners. In still other embodiments, medical gas delivery module 550 may be a standalone system that is not physically coupled to either of gas delivery system 500 or wall 601.

Figure 8:
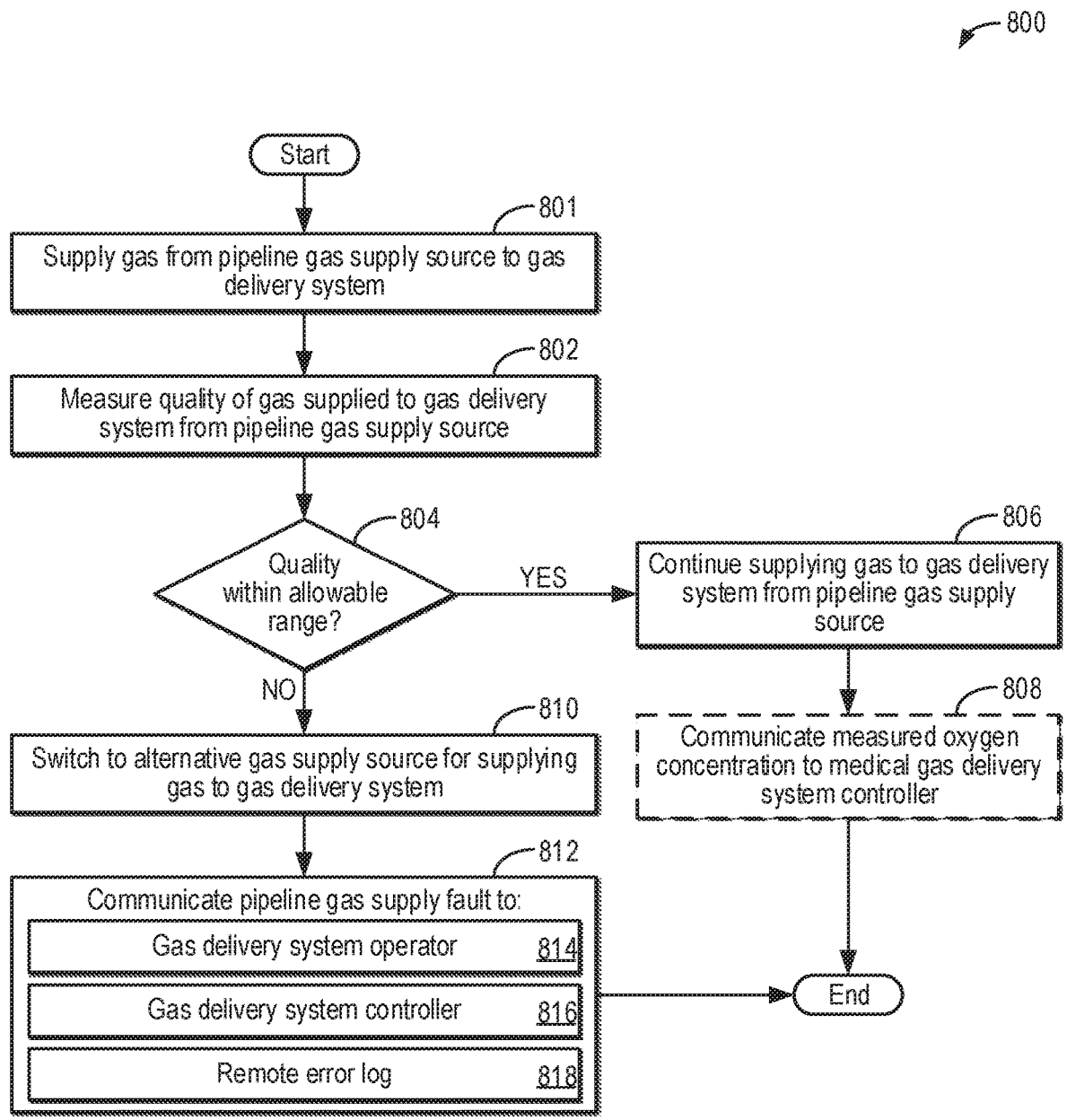
FIG. 8 is a flow chart illustrating an exemplary embodiment of a method for operating a medical gas delivery module to deliver a gas to a gas delivery system.

Turning now to FIG. 8, a method 800 is shown for operating a medical gas delivery module, such as medical gas delivery module 250 of FIG. 2, to deliver a gas to a gas delivery system (e.g., gas delivery system 200 of FIG. 2). Method 800 may be carried out by a controller, such as delivery module controller 220 of FIG. 2, according to instructions stored in a memory of the controller and in conjunction with one or more sensors (e.g., gas quality sensor 252 of FIG. 2) and actuators (e.g., valves 256 and 258 of FIG. 2). For example, in response to a determination that a gas delivered from a pipeline gas supply source (e.g., pipeline gas supply 202 of FIG. 2) is not of a desired/expected composition, such as due to contamination and/or a different gas being supplied, the controller may actuate the valves to block gas flow from the pipeline gas supply through the medical gas delivery module and enable gas flow from an alternative gas supply source (e.g., alternative gas supply 204 of FIG. 2) through the medical gas delivery module and to the gas delivery system. For simplicity, method 800 is described for supplying a single medical gas and with respect to the system shown in FIG. 2; however, it may be understood that a controller of a multi-gas delivery module (e.g., delivery module controller 520 of medical gas delivery module 550 of FIG. 5) may perform method 800 in parallel for each of a plurality of gases delivered.

At 801, a gas is supplied to the gas delivery system from the pipeline gas supply source. The gas may be any medical gas, such as medical air, oxygen, nitrogen, nitrous oxide, carbon dioxide, etc. The pipeline gas supply source may include one or more pre-filled cylinders, manifolds, pipes, valves, filters, sensors, compressors, dryers, and/or concentrators depending on the particular medical gas supplied from the pipeline gas supply source, as further described above. In particular, components of the pipeline gas supply source may be housed at a location that is remote from the medical gas delivery module and the gas delivery system (e.g., at a central medical gas distribution system), and the gas may be delivered to the medical gas delivery module via a network of conduits (e.g., pipes and tubing). The gas from the pipeline gas supply source may flow through the medical gas delivery module to the gas delivery system via a first conduit (e.g., conduit 212 of FIG. 2). In order to supply gas from the pipeline gas supply source, the controller may maintain a first valve of the medical gas delivery module (e.g., valve 256 of FIG. 2) open, the first valve coupled in the first conduit. At the same time, the controller may block gas flow from the alternative gas supply source by maintaining a second valve of the medical gas delivery module (e.g., valve 258 of FIG. 2) closed, the second valve coupled in a second conduit configured to flow gas from the alternative gas source to the gas delivery system.

At 802, a quality of the gas supplied to the gas delivery system from the pipeline gas supply source is measured. As described above with respect to FIG. 2, the gas quality may be any measurable gas quality of interest, including (but not limited to) a water vapor content (e.g., a concentration or dew point), a hydrocarbon content, a particulate content, and an oxygen content, with the particular gas quality measured based on the gas quality sensor used (e.g., a humidity sensor for measuring the water vapor content of the gas, a hydrocarbon sensor for measuring the hydrocarbon content of the gas, a particulate matter sensor for measuring the particulate content of the gas, or an oxygen sensor for measuring the oxygen content of the gas). Further, in embodiments of the medical gas delivery module that include additional gas quality sensor(s) (e.g., one or more of optional gas quality sensors 253, 254, and 255 of FIG. 2), the additional gas quality sensor(s) may each measure an additional gas quality. In this way, one or more gas qualities, depending on the configuration of the medical gas delivery module, is measured at 802.

At 804, it is determined if the gas quality (or gas qualities, such as measured at 802) is within an allowable range. The allowable range refers to a threshold range that is predetermined for each gas quality and stored in a memory of the controller. Further, the allowable range may vary for some gas qualities, such as oxygen content, based on the type (e.g., identity) of medical gas supplied and a source of the supply, whereas the allowable range for other gas qualities, such as water vapor content, hydrocarbon content, and particulate content, may be the same for each of the different medical gases, at least in some embodiments of method 800. Thus, the controller may select the appropriate allowable range from a plurality of allowable ranges stored in memory based on the medical gas being supplied, the gas quality being measured, and the source of the medical gas.

In one example, the controller may determine the medical gas being supplied based on preprogrammed instructions stored in the memory of the controller. For example, the medical gas delivery module may be configured to supply a designated medical gas from a designated gas source. As another example, the controller may determine the medical gas being supplied based on communications received from a controller of the gas delivery system (e.g., controller 240 shown in FIG. 2). For example, the controller of the gas delivery system may communicate input received from an operator of the gas delivery system concerning the medical gas being supplied. Similarly, the controller of the medical gas delivery module may determine the gas quality being measured based on known medical gas delivery module components (e.g., the installed gas quality sensor(s)) and/or preprogrammed instructions stored into the memory of the controller. In one example, the controller may determine the source of the medical gas (e.g., pre-filled cylinders or on-site generation) based on preprogrammed instructions stored into the memory of the controller, such as when the medical gas delivery module is configured to supply a designated medical gas from a designated gas source. As another example, the controller may determine the source of the medical gas based on communications received from the controller of the gas delivery system concerning the source of the medical gas.

For example, water vapor, hydrocarbons, and particulates, which may be considered contaminants, may be undesired components of all of the medical gases. Thus, the allowable range may correspond to a relatively low amount for each of the water vapor content, the hydrocarbon content, and the particulate content. As one non-limiting example, the allowable range for the water vapor content, measured as a dew point, may be between 0 and 2° C., the allowable range for the hydrocarbon content may be between 0 and 25 ppm, and the allowable range for the particulate content may be between 0 and 1 mg/m$^3$ for particulates sized 1 micron or larger. As another example, the allowable range for the oxygen content may be a narrow and relatively high, such as between 99 and 100%, when the gas is oxygen sourced from pre-filled cylinders. As another example, the allowable range for the oxygen content may be a broader relatively high range, such as between 90 and 96%, when the gas is oxygen sourced from an oxygen concentrator. As a further example, the allowable range for the oxygen content may be a narrower and lower range, such as between 19 and 24%, when the gas is medical air. As still another example, the allowable range for the oxygen content may be a narrow range and an even lower amount, such as between 0 and 1%, when the gas is nitrogen, nitrous oxide, or carbon dioxide. Thus, the controller may evaluate each of the one or more measured gas qualities against the corresponding allowable range to determine if the quality is within the allowable range.

If the gas quality is within the allowable range (e.g., all of the one or more gas qualities are within the corresponding allowable range), method 800 proceeds to 806, and the supply of the gas to the gas delivery system from the pipeline gas supply source is continued. For example, the controller may maintain the first valve of the medical gas delivery module open and maintain the second valve of the medical gas delivery module closed. In this way, the medical gas may continue to flow from the pipeline gas supply source (and not from the alternative gas supply source), through the medical gas delivery module, and to the gas delivery system.

At 808, the measured oxygen concentration is optionally communicated to the controller of the gas delivery system. For example, 808 of method 800 is included when the measured gas quality is oxygen content and the gas source is an oxygen concentrator. However, 808 may not be included in method 800 when the measured gas quality is not oxygen content or when the oxygen gas is sourced from a pre-filled cylinder (which holds 100% oxygen). The concentration of oxygen in the gas produced by the oxygen concentrator may vary within the allowable range. Thus, communicating the measured oxygen concentration to the gas delivery system controller allows the gas delivery system controller to actively compensate for different oxygen concentrations, as will be described below with respect to FIG. 9. Following 808, method 800 ends.

Returning to 804, if the gas quality is not within the allowable range (e.g., any of the one or more gas qualities is not within the corresponding allowable range), method 800 proceeds to 810, and the gas supply source is switched to the alternative gas supply source. For example, the controller may actuate the first valve of the medical gas delivery module closed to block gas flow from the pipeline gas supply source through the medical gas delivery module and to the gas delivery system. For example, the controller may energize the first valve to actuate the first valve closed. At the same time (e.g., simultaneously), the controller may actuate the second valve of the medical gas delivery module open to enable gas flow from the alternative gas supply source through the medical gas delivery system and to the gas delivery system (e.g., via the second conduit). For example, the controller may energize the second valve to actuate the second valve closed.

At 812, a pipeline gas supply fault is communicated. The communication may include one or more audible, text-based, or computer-readable messages. Further, the communication may include an indication that the pipeline gas supply fault has occurred as well as a nature of the fault, such as what contaminant has been identified (e.g., an identity and/or amount of the contaminant) or that the wrong gas composition has been detected.

Although switching to the alternative gas supply source enables uninterrupted gas delivery, the pipeline gas supply fault is communicated to the operator of the gas delivery system, as indicated at 814, so that the operator is made aware that the gas delivery system is receiving gas from the alternative gas supply source. For example, in embodiments where the alternative gas supply source is a gas-holding cylinder, the amount of gas held by the cylinder may be less than that available from the pipeline gas supply source. Therefore, communicating the pipeline gas supply fault to the operator may prompt the operator to monitor a fill amount of the cylinder, for example. As another example, communicating the pipeline gas supply fault to the operator enables the operator to select a different alternative gas source, as desired. As still another example, the operator may contact other personnel, such as other gas delivery system operators or personnel of the central medical gas distribution system, to alert them about the pipeline gas supply fault. Communicating the pipeline gas supply fault to the operator may include emitting an alarm or other audible alert, such as a spoken message, for example.

Further, the pipeline gas supply fault is communicated to the gas delivery system controller, as indicated at 816. The controller of the medical gas delivery module may transmit an electronic communication to the gas delivery system controller, for example, via wired or wireless connections. As one example, the gas delivery system controller may output an additional communication to the operator, such as an additional audible message and/or a text-based message. For example, the gas delivery system controller may output the text-based message on a display device of the gas delivery system (e.g., anesthesia display device 15 and/or patient monitoring display device 16 of FIG. 1A). As another example, the gas delivery system controller may perform a diagnostic routine to check for degradation in response to receiving the pipeline gas supply fault communication from the controller of the gas delivery system.

Additionally, the pipeline gas supply fault is communicated to a remote error log, as indicated at 818. The controller of the medical gas delivery module may transmit an electronic communication to the remote error log, for example, via wired or wireless connections. For example, the remote error log may be stored on a remote network (e.g., remote network 231 shown in FIG. 2), enabling detected pipeline gas supply faults from multiple medical gas delivery modules located throughout a facility to be logged at a single location. Further, logging the pipeline gas supply fault at the remote error log may enable cross-correlation of the pipeline gas supply fault with equipment degradation, including degradation of the gas delivery system, other gas delivery systems (including those that are not coupled to a medical gas delivery module), and any other equipment that receives gas from the pipeline gas supply (such as incubators, surgical equipment, etc.). Additionally, logging the pipeline gas supply fault at the remote error log may enable a manufacturer of the medical gas delivery module to access the remote error log for performance monitoring and maintenance. For example, the manufacturer of the medical gas delivery module and/or the gas delivery system may be pre-emptively schedule maintenance to clean or replace components of the medical gas delivery module and/or the gas delivery system, thereby avoiding or reducing degradation and decreasing an amount of time that the gas delivery system is shutdown. Method 800 may then end. In this way, an uninterrupted supply of clean medical gas having a desired composition is provided to a gas delivery system, preventing gas delivery system degradation, potentially increasing patient safety, and reducing operator frustration.

Figure 9:
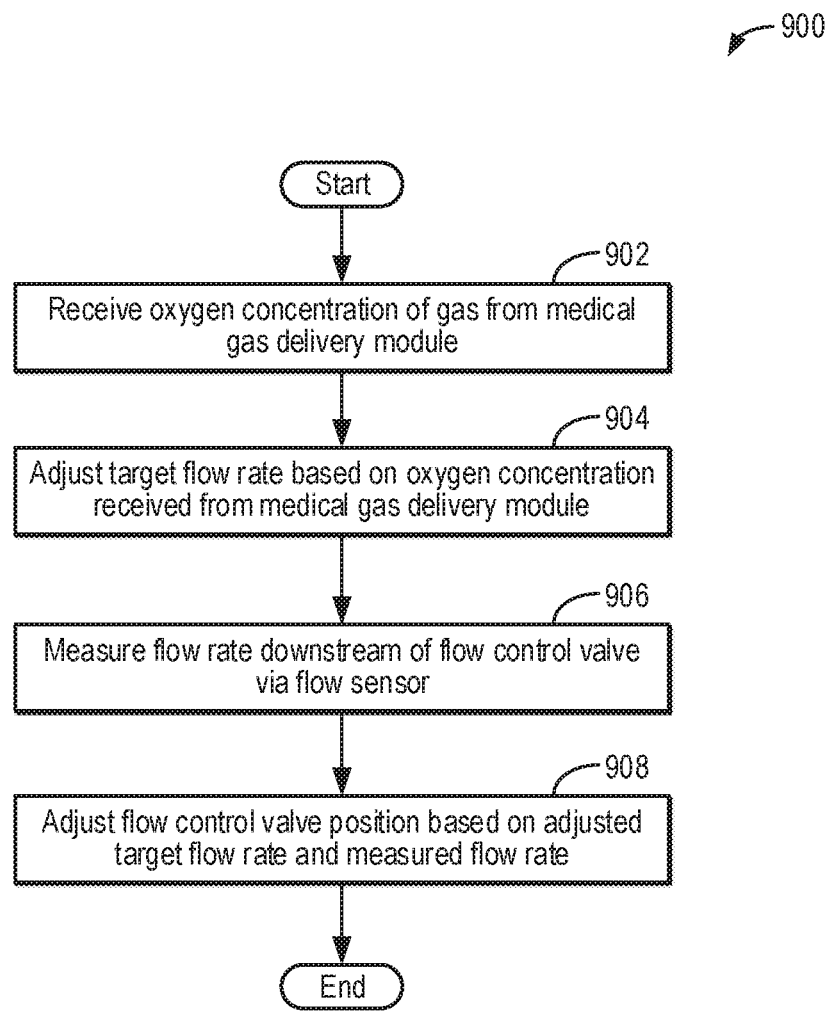
FIG. 9 is a flow chart illustrating an exemplary embodiment of a method for adjusting operation of a gas delivery system based on an oxygen concentration measured by a medical gas delivery module.

Next, FIG. 9 shows a method 900 for adjusting operation of a gas delivery system, such as gas delivery system 200 of FIG. 2 or gas delivery system 500 of FIG. 5, based on an oxygen concentration measured by a medical gas delivery module (e.g., medical gas delivery module 250 of FIG. 2 or medical gas delivery module 550 of FIG. 5) that supplies oxygen gas from a pipeline gas supply source (e.g., pipeline gas supply 202 of FIG. 2 or pipeline gas supply 502a of FIG. 5). In particular, the pipeline gas supply source includes an oxygen concentrator for generating the oxygen gas. Method 900 may be carried out by a controller, such as controller 240 of FIG. 2 or controller 540 of FIG. 5, according to instructions stored in a memory of the controller and in conjunction with one or more sensors (e.g., flow sensor 242 of FIG. 2 or flow sensor 542a of FIG. 5) and actuators (e.g., flow control valve 244 of FIG. 2 or flow control valve 544a of FIG. 5).

At 902, an oxygen concentration of the gas is received from the medical gas delivery module. As described above with respect to method 800 of FIG. 8, the medical gas delivery module may measure the oxygen concentration of the gas received from the pipeline gas supply source, and in response to the oxygen concentration being within an allowable range, communicate the measured oxygen concentration to the gas delivery system. For example, the controller may receive an electronic communication from a controller of the medical gas delivery module (e.g., delivery module controller 220 of FIG. 2 or delivery module controller 520 of FIG. 5) that indicates the oxygen concentration measured by a sensor of the medical gas delivery module.

At 904, a target flow rate is adjusted based on the oxygen concentration received from the medical gas delivery module. For example, the target flow rate may be pre-calibrated based on a target concentration of oxygen to deliver to a patient via the gas delivery system and an inferred oxygen concentration of the gas supplied to the gas delivery system. However, the actual oxygen concentration of the gas supplied to the gas delivery system may vary from the inferred oxygen concentration (but remain within the allowable range). Therefore, the controller may adjust the target flow rate based on the actual oxygen concentration measured by the medical gas delivery module. As one example, the controller may input the received oxygen concentration into a look-up table or algorithm stored in memory, which may output the adjusted target flow rate for the corresponding oxygen concentration, for example. As another example, the controller may make a logical determination (e.g., regarding the target flow rate) based on logic rules that are a function of the oxygen concentration received from the medical gas delivery module. For example, as the oxygen concentration measurement received from the medical gas delivery module decreases, the target flow rate may be increased to compensate for the decreased oxygen content of the gas, and as the oxygen concentration measurement received from the medical gas delivery module increases, the target flow rate may be decreased to compensate for the increased oxygen content of the gas. Thus, a correction or compensation may be used to account for variations in the oxygen concentration, thereby increasing an accuracy of the concentration of oxygen delivered to the patient.

At 906, a flow rate downstream of the flow control valve is measured via the flow sensor. For example, the flow sensor may provide a feedback signal to the controller so that the controller may compare the measured flow rate to the adjusted target flow rate. As one example, the controller may generate an error value as the difference between the adjusted target flow rate, which serves as a flow setpoint, and the measured flow rate.

At 908, a flow control valve position is adjusted based on the adjusted target flow rate and the measured flow rate. The flow control valve, configured to adjust the flow of the oxygen gas to downstream components of the gas delivery machine, may be adjusted to a further open position or to a further closed position to achieve or maintain the target flow rate, thereby achieving the target concentration of oxygen in the downstream flow. For example, the oxygen gas may mix with other gases downstream of the flow control valve before being delivered to the patient. As an example, the controller may input the measured flow rate and the target flow rate into a look-up table or algorithm stored in a memory of the controller, which may output the adjusted flow control valve position. As another example, the controller may be configured as a proportional-integral-derivative controller and may generate a corrective action for the flow control valve position based on the error value using proportional, integral and derivative terms in order to drive the measured flow rate to the target flow rate. The controller may then send a corresponding control signal to the flow control valve to actuate the flow control valve to the adjusted flow control valve position. For example, as the measured flow rate increases above the target flow rate, the flow control valve may be adjusted to a further closed position to further restrict gas flow through the flow control valve, and as the measured flow rate decreases below the target flow rate, the flow control valve may be adjusted to a further open position to enable additional gas flow through the valve. Method 900 may then end. In this way, an amount of oxygen in gas output by the gas delivery system may be accurately controlled.

Thus, the systems and methods described herein provide for a smart medical gas delivery module, enabling an uninterrupted supply of clean, dry medical gas of an expected composition to be delivered to a gas delivery system without human intervention. As a result, equipment and patient exposure to a contaminated or wrong medical gas is limited, thereby decreasing gas delivery system degradation and potentially increasing patient safety. By decreasing gas delivery system degradation, an amount of time that the gas delivery system is out of service is decreased and maintenance costs are decreased. Further, an accuracy of a gas mixture delivered by the gas delivery system to a patient may be increased. Overall, gas delivery system operator satisfaction may be increased.

A technical effect of monitoring a quality of a medical gas supplied from a medical gas pipeline to a gas delivery system upstream of an inlet to the gas delivery system and automatically switching to an alternative gas supply if the quality is outside of an allowable range is that degradation of the gas delivery system is decreased while the gas delivery system receives an uninterrupted supply of gas.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a medical gas delivery module, comprising:
    supplying a medical gas from a pipeline gas supply source to a gas delivery system via a first conduit;
    measuring a quality of the medical gas in the first conduit;
    comparing the measured quality to an allowable range;
    responding to the measured quality being outside of the allowable range by:
        switching to an alternative gas supply source for supplying the medical gas to the gas delivery system via a second conduit; and
        transmitting a pipeline gas supply fault to an operator of the gas delivery system, a controller of the gas delivery system, and a remote error log, wherein the pipeline gas supply fault includes one or more of an audible, text-based, or computer-readable message, and transmitting the pipeline gas supply fault to the remote error log comprises data configured for tracking the pipeline gas supply fault and enabling remote cross-correlation between pipeline supply errors and gas delivery system degradation; and
    continuing supplying the medical gas to the gas delivery system from the pipeline gas supply source in response to the measured quality being inside of the allowable range.

2. The method of claim 1, wherein measuring the quality of the medical gas in the first conduit includes measuring the quality via a gas quality sensor coupled in the first conduit, wherein the gas quality sensor is one of a humidity sensor, a hydrocarbon sensor, and a particulate matter sensor.

3. The method of claim 1, wherein supplying the medical gas from the pipeline gas supply source to the gas delivery system includes maintaining open a first valve coupled in the first conduit and maintaining closed a second valve coupled in the second conduit configured to flow the medical gas from the alternative gas supply source to the gas delivery system.

4. The method of claim 3, wherein switching to the alternative gas supply source includes closing the first valve to block a flow of the medical gas through the first conduit while opening the second valve to enable a flow of the medical gas through the second conduit.

5. The method of claim 1, wherein the medical gas is oxygen, the pipeline gas supply source includes an oxygen concentrator, and the measured quality is a concentration of oxygen, and the method further comprises:
    further in response to the measured concentration of oxygen being inside of the allowable range, communicating the measured concentration of oxygen to a controller of the gas delivery system.

6. The method of claim 1, wherein the allowable range is selected based on at least one of an identity of the medical gas, the measured quality, and a configuration of the pipeline gas supply source.

7. A system for a medical gas delivery module, comprising:
    a first conduit configured to flow a medical gas from a pipeline gas supply source to a gas delivery system;
    a first valve coupled in the first conduit that, when open, enables gas flow from the pipeline gas supply source to the gas delivery system and, when closed, blocks gas flow from the pipeline gas supply source to the gas delivery system, wherein the first valve is a normally open solenoid actuated valve that is de-energized when open and energized when closed;
    at least one gas quality sensor coupled to the first conduit upstream of the first valve;
    a second conduit configured to flow the medical gas from an alternative gas supply source to the gas delivery system;
    a second valve coupled in the second conduit that, when open, enables gas flow from the alternative gas supply source to the gas delivery system and, when closed, blocks gas flow from the alternative gas supply source to the gas delivery system, wherein the second valve is a normally closed solenoid actuated valve that is de-energized when closed and energized when open; and
    a controller storing executable instructions in non-transitory memory that, when executed, cause the controller to:
        supply the medical gas from the pipeline gas supply source to the gas delivery system via the first conduit;
        measure a quality of the medical gas in the first conduit via the at least one gas quality sensor;
        compare the quality of the medical gas measured by the at least one gas quality sensor to an allowable range;
        switch to the alternative gas supply source for supplying the medical gas to the gas delivery system and communicate a pipeline gas supply fault in response to the measured quality being outside of the allowable range; and
        continue supplying the medical gas to the gas delivery system from the pipeline gas supply source in response to the measured quality being inside of the allowable range.

8. The system of claim 7, wherein the instructions that cause the controller to supply the medical gas from the pipeline gas supply source to the gas delivery system via the first conduit include further executable instructions in non-transitory memory that, when executed, cause the controller to:
   maintain the first valve open by maintaining the first valve de-energized; and
   maintain the second valve closed by maintaining the second valve de-energized.

9. The system of claim 7, wherein the instructions that cause the controller to switch to the alternative gas supply source for supplying the medical gas to the gas delivery system include further executable instructions in non-transitory memory that, when executed, cause the controller to:
   close the first valve by energizing the first valve while simultaneously opening the second valve by energizing the second valve.

10. The system of claim 7, further comprising a third conduit that fluidly couples the medical gas delivery module to the gas delivery system, and wherein the first conduit is coupled to the third conduit downstream of the first valve and the second conduit is coupled to the third conduit downstream of the second valve.

11. The system of claim 7, wherein the gas delivery system is one of an anesthesia machine and a ventilator.

12. A non-transitory computer-readable medium comprising instructions that, when executed, cause a processor to:
   operate a medical gas delivery module to supply a medical gas from a pipeline gas supply source to a gas delivery system via a first conduit of the medical gas delivery module;
   operate a gas quality sensor coupled to the first conduit to measure a quality of the medical gas in the first conduit;
   compare the quality of the medical gas measured by the gas quality sensor to an allowable range;
   respond to the quality of the medical gas being outside of the allowable range by:
      operating the medical gas delivery module to switch to an alternative gas supply source for supplying the medical gas to the gas delivery system via a second conduit;
      transmitting a pipeline gas supply fault to an operator of the gas delivery system, a controller of the gas delivery system, and a remote error log, wherein the pipeline gas supply fault includes one or more of an audible, text-based, or computer-readable message, and transmitting the pipeline gas supply fault to the remote error log comprises data configured for tracking the pipeline gas supply fault and enabling remote cross-correlation between pipeline supply errors and gas delivery system degradation; and
   continue operating the medical gas delivery module to supply the medical gas to the gas delivery system from the pipeline gas supply source in response to the quality of the medical gas being inside of the allowable range.

13. The non-transitory computer-readable medium of claim 12, wherein to operate the medical gas delivery module to supply the medical gas from the pipeline gas supply source to the gas delivery system via the first conduit of the medical gas delivery module, the instructions, when executed, cause the processor to:
   maintain open a first valve coupled in the first conduit and maintain closed a second valve coupled in the second conduit configured to flow the medical gas from the alternative gas supply source to the gas delivery system.

14. The non-transitory computer-readable medium of claim 13, wherein to operate the medical gas delivery module to switch to the alternative gas supply source for supplying the medical gas to the gas delivery system, the instructions, when executed, cause the processor to:
   close the first valve to block a flow of the medical gas through the first conduit while opening the second valve to enable a flow of the medical gas through the second conduit.

15. The non-transitory computer-readable medium of claim 12, wherein to compare the quality of the medical gas measured by the gas quality sensor to the allowable range, the instructions, when executed, cause the processor to:
   select the allowable range based on at least one of an identity of the medical gas, the quality of the medical gas measured by the gas quality sensor, and a configuration of the pipeline gas supply source.

* * * * *